(12) United States Patent
Nishiyama et al.

(10) Patent No.: US 9,102,969 B2
(45) Date of Patent: Aug. 11, 2015

(54) METHOD FOR PRODUCING HETEROLOGOUS PROTEIN USING YEAST WITH DISRUPTION OF VPS GENE

(75) Inventors: Tozo Nishiyama, Hyogo (JP); Yasuyoshi Sakai, Kyoto (JP)

(73) Assignee: KANEKA CORPORATION, Osaka-shi (JP)

( * ) Notice: Subject to any disclaimer, the term of this patent is extended or adjusted under 35 U.S.C. 154(b) by 0 days.

(21) Appl. No.: 14/004,223

(22) PCT Filed: Mar. 7, 2012

(86) PCT No.: PCT/JP2012/055825
§ 371 (c)(1),
(2), (4) Date: Sep. 10, 2013

(87) PCT Pub. No.: WO2012/124567
PCT Pub. Date: Sep. 20, 2012

(65) Prior Publication Data
US 2014/0106404 A1    Apr. 17, 2014

(30) Foreign Application Priority Data
Mar. 11, 2011   (JP) .................. 2011-054637

(51) Int. Cl.
*C12P 21/00*     (2006.01)
*C12N 15/81*     (2006.01)
*C12N 15/67*     (2006.01)
*C07K 14/39*     (2006.01)
*C12P 21/02*     (2006.01)
*C07K 16/00*     (2006.01)

(52) U.S. Cl.
CPC .............. *C12P 21/00* (2013.01); *C07K 14/39* (2013.01); *C07K 16/00* (2013.01); *C12N 15/815* (2013.01); *C12P 21/02* (2013.01)

(58) Field of Classification Search
CPC combination set(s) only.
See application file for complete search history.

(56) References Cited

U.S. PATENT DOCUMENTS

2006/0148039 A1    7/2006   Kobayashi et al.

FOREIGN PATENT DOCUMENTS

| JP | 2009-60797 A | 3/2009 |
| JP | 2009-240185 A | 10/2009 |
| JP | 2010-193869 A | 9/2010 |

OTHER PUBLICATIONS

Abdel-Salam et al., "Expression of mouse anticreatine kinase (MAK33) monoclonal antibody in the yeast Hansenula polymorpha", Applied Microbiol Biotechnology, vol. 56, pp. 157-164, 2001, Materials and Methods.
Agaphonov et al., "Defect of vacuolar protein sorting stimulates proteolytic processing of human urokinase-type plasminogen activator in the yeast Hansenula polymorpha", FEMS Yeast Research, vol. 5, pp. 1029-1035, 2005, Materials and Methods, Table 1.
Cregg et al., "Recombinant Protein Expression in *Pichia pastoris*", Molecular Biotechnology, vol. 16, pp. 23-52, 2000, Table 1.
Idiris et al., "Enhanced protein secretion from multiprotease-deficient fission yeast by modification of its vacuolar protein sorting pathway", Applied Microbiol Biotechnology, vol. 85, pp. 667-677, 2010, Fig. 5.
International Search Report, mailed Apr. 3, 2012, issued in PCT/JP2012/055825.
Nett, "Production of Antibodies in *Pichia pastoris*", Therapeutic Monoclonal Antibodies: From Bench to Clinic, Chapter 26, pp. 573-588, 2009, lines 8 to 12.
Written Opinion of the International Searching Authority, mailed Apr. 3, 2012, issued in PCT/JP2012/055825.
Elena V. Morozkina, et al., "Proteinase B Disruption is Required for High Level Production of Human Mechano-Growth Factor in *Saccharomyces cerevisiae*," Journal of Molecular Microbiology and Biotechnology, vol. 18, No. 3, 2010, pp. 188-194, XP008172066.
European Search Report for application No. 12757313.7, dated Sep. 24, 2014.

*Primary Examiner* — Kagnew H Gebreyesus
(74) *Attorney, Agent, or Firm* — Birch, Stewart, Kolasch & Birch, LLP

(57) ABSTRACT

An object of the present invention it to improve the secretion productivity of a heterologous protein in a methanol-assimilating yeast. The present invention provides a method for producing a heterologous protein, characterized by comprising using a methanol-assimilating yeast with disruption of the VPS gene as a host for secretory production of the heterologous protein.

5 Claims, No Drawings

METHOD FOR PRODUCING HETEROLOGOUS PROTEIN USING YEAST WITH DISRUPTION OF VPS GENE

This application is the National Phase of PCT International Application No. PCT/JP2012/055825, filed on Mar. 7, 2012, which claims priority under 35 U.S.C. 119(a) to Patent Application No. 2011-054637, filed in Japan on Mar. 11, 2011, all of which are hereby expressly incorporated by reference into the present application.

TECHNICAL FIELD

The present invention relates to a method for producing a heterologous protein using a yeast host with the improved secretion productivity of a heterologous protein via disruption of the VPS gene.

BACKGROUND ART

In recent years, host strains for production of proteins of interest, such as animal cells (e.g., CHO), insects (e.g., silk worm), insect cells, animals (e.g., chickens and cows), and microorganisms (e.g., *E. coli* and yeast), have been used in order to produce proteins via genetic recombination. In particular, yeasts can be cultured in large-scale, high-density culture systems in cost-effective media, and proteins can be produced at low cost. In addition, proteins can be secreted in a culture solution of yeast cells by using a signal peptide or the like, therefore, a process for purifying proteins is easy.

When a yeast host is used, however, heterologous protein production is not always satisfactory. Thus, improvement of protein productivity has been attempted through use of a potent promoter or improvement, such as reinforcement of chaperon functions via introduction of the chaperon gene, or disruption of a protease gene possessed by a yeast host.

Concerning heterologous protein secretion into a culture solution, an improvement in the productivity achieved via disruption of the vacuolar protein sorting (VPS) gene was reported in addition to the improvement described above.

While 61 types of VPS genes denoted as VPS1 to VSP75 are known to exist in the budding yeast *Saccharomyces cerevisiae*, all of such VPS genes are not effective. It is reported that the secretion productivity of a heterologous protein is improved via disruption of the particular VPS gene (Non-Patent Document 1; Patent Documents 1, 2, and 3).

In addition, genes that are effective to achieve the improved secretion productivity of a heterologous protein vary depending on yeast species. For example, disruption of the VPS10 gene is effective for the fission yeast *Schizosaccharomyces pombe* (Non-Patent Document 1), although such disruption is not effective for the budding yeast *Saccharomyces cerevisiae* (Patent Document 1).

PRIOR ART DOCUMENTS

Patent Documents

Patent Document 1: JP 2009-60797 A
Patent Document 2: JP 2009-240185 A
Patent Document 3: JP 2010-193869 A

Non-Patent Document

Non-Patent Document 1: Alimjan, I. Appl. Microbiol. Biotechnol., 2010, vol. 85, pp. 667-677

SUMMARY OF THE INVENTION

Problem to be Solved by the Invention

The influence of disruption of the VPS gene imposed on secretory production of a heterologous protein in a methanol-assimilating yeast having properties significantly different from those of the budding yeast *Saccharomyces cerevisiae* or the fission yeast *Schizosaccharomyces pombe* was unknown. Accordingly, it is an object of the present invention to discover an effective VPS gene to be disrupted in a methanol-assimilating yeast, and to improve the secretion productivity of heterologous protein.

Means for Solving the Problem

The present invention includes the following inventions.
(1) A method for producing a heterologous protein, characterized by comprising using methanol-assimilating yeast with disruption of the VPS gene as a host for secretory production of the heterologous protein.
(2) The method according to (1), characterized by comprising using a methanol-assimilating yeast with disruption of the PRB1 gene simultaneously with the VPS gene as a host for secretory production of a heterologous protein.
(3) The method according to (1) or (2), wherein the methanol-assimilating yeast is a transformant of the genus *Pichia*.
(4) The method according to (3), wherein the yeast of the genus *Pichia* is selected from the group consisting of *Pichia angsta, Pichia methanolica, Pichia minuta*, and *Pichia pastoris*.
(5) The method according to any of (1) to (4), wherein the VPS gene is at least one gene selected from the group consisting of VPS5, VPS6, VPS8, VPS10, VPS15, VPS17, VPS21, VPS26, VPS29, VPS34, VPS35, and VPS45.
(6) The method according to any of (1) to (5), wherein the heterologous protein is a human or animal therapeutic protein.
(7) The method according to any of (1) to (6), wherein the heterologous protein is an antibody or antibody fragment.

This patent application claims priority from Japanese Patent Application No. 2011-054637 filed on Mar. 11, 2011, and includes part or all of the contents as disclosed in the description thereof.

Effects of the Invention

The present invention provides a method for producing a heterologous protein using a yeast host with the improved secretion productivity of a heterologous protein via disruption of the VPS gene.

EMBODIMENTS FOR CARRYING OUT THE INVENTION

The "methanol-assimilating yeast" of the present invention can grow with the use of methanol as a sole carbon source. Examples of preferable yeasts are those belonging to the genus *Pichia* or *Candida*. More preferably, such yeasts are, for example, *Pichia pastoris, Pichia angsta, Pichia methanolica, Pichia minuta*, or *Candida boidinii*.

Examples of preferable *Pichia angusta* strains include, but are not particularly limited to, NCYC495 (ATCC14754), 8V (ATCC34438), and DL-1 (ATCC26012). Such strains can be obtained from the American Type Culture Collection or other institutions. Strains derived from such strains can also be used, and examples of leucine auxotrophs include NCYC495-derived BY4329, 8V-derived BY5242, and DL-1-derived BY5243. These strains can be distributed by the National BioResource Project.

Examples of preferable *Pichia pastoris* strains include, but are not particularly limited to, Y-11430 and X-33. Such strains can be obtained from the Northern Regional Research Laboratory or other institutions. Strains derived from such strains can also be used.

Examples of preferable *Pichia minuta* strains include, but are not particularly limited to, NBRC1473, NBRC0975, NBRC10402, and NBRC10746.

Examples of preferable *Pichia methanolica* strains include, but are not particularly limited to, NBRC1909, NBRC10704, and NBRC101503.

Examples of *Candida boidinii* strains include, but are not particularly limited to, NBRC1967, NBRC10035, NBRC10240, NBRC10329, NBRC10574, NBRC10871, NBRC101490, and NBRC101491. These strains can be obtained from the NITE Biological Resource Center or other institutions. Strains derived from such strains can also be used.

The "heterologous protein" of the present invention is not particularly limited, and it can be, for example, an enzyme derived from a microorganism or a protein produced by a multicellular organism, such as an animal or plant. Examples thereof include phytase, protein A, protein G, protein L, amylase, glucosidase, cellulase, lipase, protease, glutaminase, peptidase, nuclease, oxidase, lactase, xylanase, trypsin, pectinase, isomerase, and fluorescent protein. Preferable examples include human or animal therapeutic proteins.

Specific examples of human or animal therapeutic proteins include hepatitis B virus surface antigen, hirudin, antibody, partial antibody, serum albumin, epidermal growth factor, insulin, growth hormone, erythropoietin, interferon, antihemophilic factor, granulocyte colony-stimulating factor (G-CSF), granulocyte-macrophage colony-stimulating factor (GM-CSF), thrombopoietin, IL-1, IL-6, tissue plasminogen activator (TPA), urokinase, leptin, and stem cell growth factor (SCF). An antibody and a partial antibody are particularly preferable.

The term "antibody" refers to a heterotetrameric protein composed of two L- and H-polypeptide chains joined by disulfide bonds. An antibody is not particularly limited, provided that it is capable of binding to a particular antigen.

The term "partial antibody" refers to Fab antibody, $(Fab)_2$ antibody, scFv antibody, diabody antibody, or a derivative of any thereof. A partial antibody is not particularly limited, provided that it is capable of binding to a particular antigen. The term "Fab antibody" refers to a heteromeric protein comprising the L-chain and the Fd chain of the antibody joined by S—S bonds or a heteromeric protein comprising the L-chain and the Fd chain of the antibody joined with each other without S—S bonds. A Fab antibody is not particularly limited, provided that it is capable of binding to a particular antigen.

The heterologous protein as mentioned above may originate from any animals without particular limitation. Examples thereof include humans, mice, rats, chickens, and camels. Alternatively, the heterologous protein may be a chimeric protein originating from two or more such animals.

A host for secretory production of such heterologous protein can be prepared by transforming the host with a vector for secretory expression of a heterologous protein via genetic engineering.

The term "secretory production" used in the present invention refers to heterologous protein accumulation resulting from liquid culture of methanol-assimilating yeast in the culture supernatant instead of the inside of the yeast. Secretory production is carried out by allowing a heterologous protein to express in the form of a fusion protein with a secretory signal, and fusion is realized by, for example, introducing a nucleotide sequence encoding a signal sequence into the 5' end of a nucleotide sequence encoding the heterologous protein.

A nucleotide sequence encoding a signal sequence is not particularly limited, provided that a methanol-assimilating yeast is capable of secreting the heterologous protein. Examples thereof include nucleotide sequences encoding signal sequences of the mating factor α (MFα) of *Saccharomyces cerevisiae*, acid phosphatase (PHO1) of *Pichia angusta*, acid phosphatase (PHO1) of *Pichia pastoris*, invertase (SUC2) of *Saccharomyces cerevisiae*, PLB1 of *Saccharomyces cerevisiae*, bovine serum albumin (BSA), human serum albumin (HSA), and immunoglobulin.

The term "host for secretory production" used in the present invention refers to a host that can produce heterologous protein at high levels through introduction of an expression vector for secretory production of a heterologous protein thereinto. The host is characterized in that the VPS gene is disrupted.

The term "expression vector for secretory production of a heterologous protein" refers to a nucleic acid molecule having a function of expressing a target gene in a transformed host cell. The expression vector has, for example, an expression cassette, a homologous recombination region, a selection marker gene, such as an auxotrophic complementary gene or drug tolerant gene, and an autonomously replicating sequence.

The vector after transformation may be integrated into the chromosome, or it may be present in the form of an autonomously replicating vector. Examples of autonomously replicating vectors include the YEp vector, the YRp vector, and the YCp vector. In the case of the genus *Pichia*, examples of vectors include, but are not particularly limited to, the pPI-CHOLI, pHIP, pHRP, and pHARS vectors.

The "expression cassette" is composed of a promoter and the heterologous protein gene, and it may comprise a terminator gene. A secretory signal may be a signal of the heterologous protein. Alternatively, a secretory signal that can function in a host may be fused to the heterologous protein. The expression cassette can be constructed in, for example, a plasmid such as pUC19, or it can be prepared via PCR.

Examples of techniques of yeast transformation include known techniques such as electroporation, the lithium acetate method, and the spheroplast method, although the techniques are not limited thereto.

For example, *Pichia angusta* is generally transformed via electroporation as described in "Highly-efficient electrotransformation of the yeast *Hansenula polymorpha*" (Curr. Genet., 25: 305.310.).

The term "the VPS gene" used in the present invention refers to a gene encoding a protein associated with the mechanism of protein transport to the vacuole in a methanol-assimilating yeast. More specifically, the term "VPS genes" refers to orthologous genes of the methanol-assimilating yeast corresponding to 61 types of vacuolar protein sorting (VPS) genes denoted as VPS1 to VPS 75 in *Saccharomyces cerevisiae*. In addition, genes that are defined to encode proteins associated with the mechanism of protein transport to the vacuole in a methanol-assimilating yeast are within the scope of the VPS genes according to the present invention, although such genes do not exist in *Saccharomyces cerevisiae*.

The term "orthologous genes" refers to a group of different types of genes, which are evolved from a common progenitor gene and have same functions. Thus, the degree of sequence identity between orthologous genes is not particularly limited, provided that the genes are equivalent to each other from the viewpoint of functions and evolutionary development. For example, orthologous genes have 30% or higher, preferably 50% or higher, more preferably 70% or higher, and further preferably 90% or higher sequence identity, at the amino acid level.

In the present invention, a single type of VPS gene may be disrupted, or a plurality of VPS genes may be disrupted, provided that the secretion productivity of a heterologous protein is improved. If the secretion productivity is improved by disrupting the VPS gene simultaneously with other genes, such combination of genes is within the scope of the present invention.

Examples of other genes to be disrupted simultaneously with the VPS gene include genes that encode vacuole protease, such as carboxypeptidase Y, that is abnormally secreted extracellularly upon disruption of the VPS gene. Through disruption of the vacuole protease gene, decomposition of the heterologous protein that had been secreted can be suppressed.

Examples of vacuole protease genes include orthologous genes of a methanol-assimilating yeast corresponding to genes of *Saccharomyces cerevisiae* designated as "PRB1."

Effects for improving secretion productivity can be evaluated by introducing a vector for secretory expression of a heterologous protein into a strain before gene disruption and a gene disruption strain, respectively, culturing the resulting transformed strains under the same conditions (e.g., liquid culture), and comparing the concentrations of heterologous proteins accumulated in a culture supernatant. Alternatively, the total amount of heterologous protein contained in a culture solution is divided by the amount of the yeast cells cultured (i.e., OD or a dry cell weight), and the production amounts of heterologous protein per cell may be compared.

The term "gene disruption" used herein refers to loss of gene functions or a significant reduction in such functions. When the VPS gene is disrupted, for example, the gene product thereof is not expressed at all. Even if the gene product of the VPS gene is expressed, it may not function normally as VPS. Such gene disruption is achieved through modification (i.e., disruption, substitution, addition, or insertion) of nucleotides in an ORF of the gene and/or modification (i.e., disruption, substitution, addition, or insertion) of nucleotides in a region where initiation or termination of transcription is controlled, such as a promoter, enhancer, or terminator region. A site and a sequence subjected to disruption, substitution, addition, or insertion are not particularly limited, provided that normal functions of the gene of interest are deprived.

In the present invention, a method for preparing a gene disruption strain is not particularly limited. For example, a vector for gene disruption comprising a partial or full-length VPS gene sequence and a selection marker may be used to introduce the vector into a site in the vicinity of the target VPS gene via homologous recombination. Alternatively, non-homologous recombination or treatment with a mutagen may be performed.

In the present invention, the VPS gene to be disrupted is not particularly limited, provided that the amount of heterologous protein produced and secreted by a methanol-assimilating yeast is increased. In terms of high effects of improved secretion productivity of a heterologous protein, disruption of the VPS5, VPS6, VPS8, VPS10, VPS15, VPS17, VPS21, VPS26, VPS29, VPS34, VPS35, or VPS45 gene is preferable, disruption of the VPS8, VPS10, VPS15, VPS17, VPS21, VPS26, or VPS45 gene is more preferable, and disruption of the VPS8, VPS10, or VPS15 gene is the most preferable. One of the above VPS genes may be subjected to disruption alone or two or more thereof may be subjected to disruption in combination.

An example of a method for heterologous protein secretion using the host for secretory production of the present invention is a method comprising culturing the host for secretory production and allowing heterologous proteins to accumulate in the culture supernatant.

A host for secretory production can be generally cultured with the use of any medium containing a nutrient source that can be utilized by a methanol-assimilating yeast.

For example, a common medium obtained by adequately mixing carbon sources, such as sugars (e.g., glucose, sucrose, and maltose), organic acids (e.g., lactic acid, acetic acid, citric acid, and propionic acid), alcohols (e.g., methanol, ethanol, and glycerol), carbohydrates (e.g., paraffin), fats and oils (e.g., soybean oil and rapeseed oil), or mixtures of any thereof, nitrogen sources, such as ammonium sulfate, ammonium phosphate, urea, yeast extract, meat extract, peptone, and corn steep liquor, and other nutrient sources, such as inorganic salts and vitamins, can be used, and culture can be carried out in a batch or continuous system.

A heterologous protein produced with the use of the host for secretory production of the present invention may be present in a culture supernatant, or a protein may be isolated therefrom via any technique. A protein can be isolated from a culture supernatant by performing known protein purification techniques in adequate combination.

For example, the host for secretory production is first cultured in an adequate medium, and a culture solution is subjected to centrifugation or filtration to remove yeast from the culture supernatant. The obtained culture supernatant is then subjected to techniques such as salting-out (e.g., ammonium sulfate precipitation or sodium phosphate precipitation), solvent precipitation (e.g., protein fractional precipitation with acetone or ethanol), dialysis, gel filtration chromatography, ion-exchange chromatography, hydrophobic chromatography, affinity chromatography, reverse phase chromatography, or ultrafiltration. Any such techniques may be carried out alone or in combination, and the heterologous protein of the present invention is isolated from the culture supernatant.

The isolated heterologous protein can be used without processing. Alternatively, such heterologous protein may be subjected to pharmacological modification such as PEGylation, modification for the purpose of impartation of enzyme or isotope functions, or other types of modification before use. Also, proteins may be used in various forms of formulations.

EXAMPLES

Hereafter, the present invention is described in greater detail with reference to the examples, although the present invention is not limited thereto. The recombinant DNA technology employed in the examples below is specifically described in the following books: Molecular Cloning 2nd Edition, Cold Spring Harbor Laboratory Press, 1989; and Current Protocols in Molecular Biology, Greene Publishing Associates and Wiley-Interscience.

Plasmids obtained in the examples below were amplified using transformants obtained with the use of *E. coli* DH5α competent cells (Takara Bio Inc.) under the designated conditions.

PCR was carried out using the Prime STAR HS DNA Polymerase (Takara Bio Inc.) in accordance with the manufacturer's instructions. Genomic DNAs were prepared from yeasts using Dr. GenTLE® (Takara Bio Inc.) in accordance with the manufacturer's instructions.

The MOX promoter (SEQ ID NO: 1), the MOX terminator (SEQ ID NO: 2), the LEU2 gene (SEQ ID NO: 3), and the GAP promoter (SEQ ID NO: 4) used when constructing the antibody-expressing vector and the vector for VPS gene disruption were prepared by PCR using genomic DNA of the *Pichia angsta* 8V strain as the template.

The mating factor α pre-pro signal gene (MFα, SEQ ID NO: 5) was prepared by PCR using genomic DNA of *Saccharomyces cerevisiae* S288c as a template. The antibody gene was prepared by PCR using, as templates, the L-chain gene (SEQ ID NO: 6) and the H-chain gene (SEQ ID NO: 7) chemically synthesized based on the disclosed sequence information of the fully humanized anti-TNF-α antibody (adalimumab; HUMIRA®) (JP 2009-082033 A). The G418 tolerant gene (SEQ ID NO: 8) was prepared by PCR using, as a template, pMW218 (Nippon Gene). The zeocin tolerant gene (SEQ ID NO: 52) was prepared by PCR using, as a template, pPICZα (Invitrogen). The VPS8 gene (SEQ ID NO: 9), the VPS10 gene (SEQ ID NO: 10), the VPS15 gene (SEQ ID NO: 11), the VPS17 gene (SEQ ID NO: 12), the VPS21 gene (SEQ ID NO: 13), the VPS26 gene (SEQ ID NO: 14), the VPS45 gene (SEQ ID NO: 15), and the PRB1 gene (SEQ ID NO: 53) were prepared by PCR using, as a template, genomic DNA of the *Pichia angsta* NCYC495 strain.

Example 1

Construction of Fab Antibody-Expressing Vector

A gene fragment (SEQ ID NO: 16) having the HindIII-NotI-BamHI-SpeI-MunI-BglII-XbaI-EcoRI sites was fully synthesized, and the resultant was inserted into the HindIII and EcoRI sites of pUC19 to prepare pUC-1.

A gene fragment having the HindIII sites on both sides of the LEU2 was prepared by PCR using the primers 1 and 2 (SEQ ID NOs: 17 and 18), the fragment was treated with HindIII, and it was then inserted into the HindIII site of pUC-1 to prepare pUC-2.

Subsequently, a gene fragment having the BamHI sites on both sides of the MOX promoter was prepared by PCR using the primers 3 and 4 (SEQ ID NOs: 19 and 20), the fragment was treated with BamHI, and it was then inserted into the BamHI site of pUC-2 to prepare pUC-3.

A gene fragment having the MunI sites on both sides of the MOX promoter was prepared by PCR using the primers 5 and 6 (SEQ ID NOs: 21 and 22), the fragment was treated with MunI, and it was then inserted into the MunI site of pUC-3 to prepare pUC-4.

A gene fragment having the XbaI site on both sides of the MOX terminator was prepared by PCR using the primers 7 and 8 (SEQ ID NOs: 23 and 24), the fragment was treated with XbaI, and it was then inserted into the XbaI site of pUC-4 to prepare pUC-PmPmTm.

A gene fragment having the SpeI site in a site upstream of MFα was prepared by PCR using the primers 9 and 10 (SEQ ID NOs: 25 and 26). A gene fragment having a 20-bp 3'-terminal fragment of MFα in a site upstream of the L-chain and the SpeI site in a site downstream of the L-chain was prepared by PCR using the primers 11 and 12 (SEQ ID NOs: 27 and 28). These gene fragments were mixed to prepare a template, and PCR was carried out using the resulting template and the primers 9 and 12 to prepare a gene fragment having the SpeI sites on both sides of a fusion gene of MFα and the L-chain.

The resulting gene fragment was treated with SpeI and inserted into the SpeI site of pUC-PmPmTm to prepare pUC-PmLPmTm.

A gene fragment having the BglII site in a site upstream of MFα was prepared by PCR using the primer 13 (SEQ ID NO: 29) and the primer 10. A gene fragment having a 20-bp 3'-terminal fragment of MFα in a site upstream of the Fd-chain and the BglII site in a site downstream of the Fd-chain was prepared by PCR using the primers 14 and 15 (SEQ ID NOs: 30 and 31). These gene fragments were mixed to prepare a template, and PCR was carried out using the resulting template and the primers 13 and 15 to prepare a gene fragment having the BglII sites on both sides of a fusion gene of MFα and the Fd-chain. The resulting gene fragment was treated with BglII and inserted into the BglII site of pUC-PmLPmTm to prepare pUC-PmLPmFTm.

This expression vector is designed to allow expression of the L-chain and the Fd-chain of the Fab antibody under the control of the different MOX promoters.

Example 2

Development of Fab Antibody-Expressing Strain

The Fab antibody-expressing vector prepared in Example 1 was cleaved at the EcoRV or NruI site in the MOX terminator gene to prepare a linearized fragment, and *Pichia angsta* was transformed using the resulting fragment. Transformation was carried out as described below.

*Pichia angsta* BY4329 cells (NCYC495-derived, leu1-1) were inoculated into 3 ml of YPD medium (1% Bacto Yeast Extract (Difco), 2% Bacto Tryptone (Difco), and 2% glucose) and subjected to shake culture at 37° C. overnight to obtain a pre-culture solution. The obtained pre-culture solution (500 μl) was inoculated into 50 ml of YPD medium, shake culture was conducted at 30° C. until OD 600 reached 1 to 1.5, and the culture product was centrifuged at 3,000×g and 20° C. for 10 minutes to harvest cells.

The cells were suspended in 10 ml of 50 mM potassium phosphate buffer (pH 7.5) containing 250 μl of 1M DTT (final concentration: 25 mM), and the suspension was incubated at 37° C. for 15 minutes. After the cells were harvested by centrifugation at 3,000×g and 4° C. for 10 minutes, the cells were resuspended in 50 ml of ice-cooled STM buffer (270 mM sucrose, 10 mM Tris-HCl, and 1 mM magnesium chloride; pH 7.5). After the cells were harvested by centrifugation at 3,000×g and 4° C. for 10 minutes, the cells were resuspended in 25 ml of ice-cooled STM buffer. After the cells were harvested by centrifugation at 3,000×g and 4° C. for 10 minutes, the cells were suspended in 250 μl of ice-cooled STM buffer, and the resulting suspension was designated as a competent cell solution.

The competent cell solution (60 μl) was mixed with 3 μl of a solution of linearized Fab antibody-expressing vector (the amount of DNA: 0.5 to 1 μg), and the mixture was transferred into an electroporation cuvette (a disposable cuvette; electrode gap: 2 mm; BM Equipment Co., Ltd.) and subjected to electroporation at 7.5 kV/cm, 10 μF, and 900Ω. Thereafter, cells were suspended in 1 ml of YPD medium, and the suspension was then allowed to stand at 37° C. for 1 hour. Thereafter, cells were harvested by centrifugation at 3,000×g at room temperature for 5 minutes, the harvested cells were washed in 1 ml of YNB medium (0.67% yeast nitrogen base (Difco), 1% glucose), and the cells were harvested from the suspension again by centrifugation at 3,000×g at room temperature for 5 minutes. The cells were suspended in an adequate amount of YNB medium, the resulting cell suspension was applied to the YNB selection agar plate, and the cells grown as a result of stationary culture at 37° C. for 3 days were selected. Thus, Fab antibody-expressing strains were obtained.

Example 3

VPS8 Gene Disruption

A fragment having the SpeI sites in sites upstream and downstream of a sequence of nucleotides 989 to 3395 of the VPS8 ORF (SEQ ID NO: 9) was prepared by PCR using primers 16 and 17 (SEQ ID NOs: 32 and 33). The resulting gene fragment was treated with SpeI and inserted into the SpeI site of pUC-1 to prepare pUC-VPS8.

A fragment having the HindIII site in a site upstream of the GAP promoter and the 5'-terminal sequence of the G418 tolerant gene in a site downstream of the GAP promoter was prepared by PCR using primers 18 and 19 (SEQ ID NOs: 34 and 35). A fragment having the HindIII site in a site downstream of the G418 tolerant gene was prepared by PCR using primers 20 and 21 (SEQ ID NOs: 36 and 37). With the use of these two fragments as templates and primers 18 and 21, PCR was carried out to obtain a fragment having the HindIII sites in sites upstream and downstream of the G418 tolerant gene under the control of the GAP promoter.

The G418 tolerant gene was inserted into the HindIII site in the VPS8 gene of pUC-VPS8 to prepare pUC-Δvps8. pUC-Δvps8 was treated with SpeI to construct a vector for VPS8 gene disruption having the G418 tolerant gene inserted into the HindIII site of the sequence comprising nucleotides 989 to 3395 of the VPS8 gene.

The resulting vector for VPS8 gene disruption was used to transform the Fab antibody-expressing strain described in Example 2, and colonies were selected on the YNB plate containing G418 at 0.5 g/l. PCR was carried out to confirm that the vector for gene disruption had been inserted into the VPS8 gene, and the Fab antibody-expressing strain with disruption of the VPS8 gene was obtained.

Example 4

VPS 10 Gene Disruption

A fragment having the SpeI sites in sites upstream and downstream of a sequence of nucleotides 3029 to 4484 of the VPS10 ORF (SEQ ID NO: 10) was prepared by PCR using primers 22 and 23 (SEQ ID NOs: 38 and 39). The resulting gene fragment was treated with SpeI and inserted into the SpeI site of pUC-1 to prepare pUC-VPS 10.

A fragment having the Bsp1407I site in a site upstream of the GAP promoter and the 5'-terminal sequence of the G418 tolerant gene in a site downstream of the GAP promoter was prepared by PCR using the primer 24 (SEQ ID NO: 40) and the primer 19. A fragment having the Bsp1407I site in a site downstream of G418 tolerant gene was prepared by PCR using the primer 20 and the primer 25 (SEQ ID NO: 41). With the use of these two fragments as templates and primers 24 and 25, PCR was carried out to obtain a fragment having the Bsp1407I sites in sites upstream and downstream of the G418 tolerant gene under the control of the GAP promoter.

The G418 tolerant gene was inserted into the Bsp1407I site in the VPS10 gene of pUC-VPS10 to prepare pUC-Δvps10. pUC-Δvps10 was treated with SpeI to construct a vector for VPS10 gene disruption comprising the G418 tolerant gene inserted into the Bsp1407I site of the sequence comprising nucleotides 3029 to 4484 of the VPS10 gene.

The resulting vector for VPS10 gene disruption was used to transform the Fab antibody-expressing strain described in Example 2, and colonies were selected on the YNB plate containing G418 at 0.5 g/l. PCR was carried out to confirm that the vector for gene disruption had been inserted into the VPS 10 gene, and the Fab antibody-expressing strain with disruption of the VPS10 gene was obtained.

Example 5

VPS15 Gene Disruption

A fragment having the SpeI sites in sites upstream and downstream of a sequence of nucleotides 506 to 2112 of the VPS15 ORF (SEQ ID NO: 11) was prepared by PCR using primers 26 and 27 (SEQ ID NOs: 42 and 43). The resulting gene fragment was treated with Spa and inserted into the SpeI site of pUC-1 to prepare pUC-VPS15.

The G418 tolerant gene prepared in Example 4 was inserted into the Bsp1407I site in the VPS15 gene of pUC-VPS15 to prepare pUC-Δvps15. pUC-Δvps15 was treated with SpeI to construct a vector for VPS15 gene disruption comprising the G418 tolerant gene inserted into the Bsp1407I site of the sequence comprising nucleotides 506 to 2112 of the VPS15 gene.

The resulting vector for VPS15 gene disruption was used to transform the Fab antibody-expressing strain described in Example 2, and colonies were selected on the YNB plate containing G418 at 0.5 g/l. PCR was carried out to confirm that the vector for gene disruption had been inserted into the VPS15 gene, and the Fab antibody-expressing strain with disruption of the VPS 15 gene was obtained.

Example 6

VPS17 Gene Disruption

A fragment having the SpeI sites in sites upstream and downstream of a sequence of nucleotides 106 to 1512 of the VPS17 ORF (SEQ ID NO: 12) was prepared by PCR using primers 28 and 29 (SEQ ID NOs: 44 and 45). The resulting gene fragment was treated with SpeI and inserted into the SpeI site of pUC-1 to prepare pUC-VPS17.

The G418 tolerant gene prepared in Example 4 was inserted into the Bsp1407I site in the VPS17 gene of pUC-VPS17 to prepare pUC-Δvps17. pUC-Δvps17 was treated with SpeI to construct a vector for VPS 17 gene disruption comprising the G418 tolerant gene inserted into the Bsp1407I site of the sequence comprising nucleotides 106 to 1512 of the VPS17 gene.

The resulting vector for VPS17 gene disruption was used to transform the Fab antibody-expressing strain described in Example 2, and colonies were selected on the YNB plate containing G418 at 0.5 g/l. PCR was carried out to confirm that the vector for gene disruption had been inserted into the VPS17 gene, and the Fab antibody-expressing strain with disruption of the VPS17 gene was obtained.

Example 7

VPS21 Gene Disruption

A fragment having the SpeI sites in sites upstream and downstream of a sequence of nucleotides 31 to 605 of the VPS21 ORF (SEQ ID NO: 13) was prepared by PCR using primers 30 and 31 (SEQ ID NOs: 46 and 47). The resulting gene fragment was treated with SpeI and inserted into the SpeI site of pUC-1 to prepare pUC-VPS21.

The G418 tolerant gene prepared in Example 3 was inserted into the HindIII site in the VPS21 gene of pUC-VPS21 to obtain pUC-Δvps21. pUC-Δvps21 was treated with SpeI to construct a vector for VPS21 gene disruption comprising the G418 tolerant gene inserted into the HindIII site of the sequence comprising nucleotides 31 to 605 of the VPS21 gene.

The resulting vector for VPS21 gene disruption was used to transform the Fab antibody-expressing strain described in Example 2, and colonies were selected on the YNB plate containing G418 at 0.5 g/l. PCR was carried out to confirm that the vector for gene disruption had been inserted into the VPS21 gene, and the Fab antibody-expressing strain with disruption of the VPS21 gene was obtained.

Example 8

VPS26 Gene Disruption

A fragment having the SpeI sites in sites upstream and downstream of a sequence of nucleotides 31 to 882 of the VPS26 ORF (SEQ ID NO: 14) was prepared by PCR using primers 32 and 33 (SEQ ID NOs: 48 and 49). The resulting gene fragment was treated with SpeI and inserted into the SpeI site of pUC-1 to prepare pUC-VPS26.

The G418 tolerant gene under the control of the GAP promoter prepared in Example 4 was inserted into the Bsp1407I site in the VPS26 gene of pUC-VPS26 to prepare pUC-Δvps26. pUC-Δvps26 was treated with SpeI to construct a vector for VPS26 gene disruption comprising the G418 tolerant gene inserted into the Bsp1407I site of the sequence comprising nucleotides 31 to 882 of the VPS26 gene.

The resulting vector for VPS26 gene disruption was used to transform the Fab antibody-expressing strain described in Example 2, and colonies were selected on the YNB plate containing G418 at 0.5 g/l. PCR was carried out to confirm that the vector for gene disruption had been inserted into the VPS26 gene, and the Fab antibody-expressing strain with disruption of the VPS26 gene was obtained.

Example 9

VPS45 Gene Disruption

A fragment having the SpeI sites in sites upstream and downstream of a sequence of nucleotides 647 to 1697 of the VPS45 ORF (SEQ ID NO: 15) was prepared by PCR using primers 34 and 35 (SEQ ID NOs: 50 and 51). The resulting gene fragment was treated with SpeI and inserted into the SpeI site of pUC-1 to prepare pUC-VPS45.

The G418 tolerant gene prepared in Example 4 under the control of the GAP promoter was inserted into the Bsp1407I site in the VPS45 gene of pUC-VPS45 to prepare pUC-Δvps45. pUC-Δvps45 was treated with SpeI to construct a vector for VPS45 gene disruption comprising the G418 tolerant gene inserted into the Bsp1407I site of the sequence comprising nucleotides 647 to 1697 of the VPS45 gene.

The resulting vector for VPS45 gene disruption was used to transform the Fab antibody-expressing strain described in Example 2, and colonies were selected on the YNB plate containing G418 at 0.5 g/l. PCR was carried out to confirm that the vector for gene disruption had been inserted into the VPS45 gene, and the Fab antibody-expressing strain with disruption of the VPS45 gene was obtained.

Example 10

PRB1 Gene Disruption

A fragment having the SpeI sites in sites upstream and downstream of a sequence of nucleotides 51 to 1400 of the PRB1 ORF (SEQ ID NO: 53) was prepared by PCR using primers 36 and 37 (SEQ ID NOs: 54 and 55). The resulting gene fragment was treated with SpeI and inserted into the SpeI site of pUC-1 to prepare pUC-PRB1.

A zeocin tolerant gene fragment was prepared by PCR using primers 38 and 39 (SEQ ID NOs: 56 and 57).

The zeocin tolerant gene fragment prepared above was inserted into the EcoRV site in the PRB1 gene of pUC-PRB1 to prepare pUC-Δprb1. pUC-Δprb1 was treated with SpeI to construct a vector for PRB1 gene disruption comprising the zeocin tolerant gene inserted into the EcoRV site of the sequence comprising nucleotides 51 to 1400 of the PRB1 gene.

The resulting vector for PRB1 gene disruption was used to transform the Fab antibody-expressing strain described in Example 2 and the Fab antibody-expressing strains with disruption of the VPS (VPS8, VPS10, and VPS15) genes described in Examples 3 to 5, and colonies were selected on the YNB plate containing zeocin at 0.1 g/l. PCR was carried out to confirm that the vector for gene disruption had been inserted into the PRB1 gene, and the Fab antibody-expressing strain with disruption of the PRB1 gene and the Fab antibody-expressing strain with double disruption of the PRB1 and VPS genes were obtained.

Comparative Example 1

PEP4 Gene Disruption

A fragment having the SpeI sites in sites upstream and downstream of a sequence of nucleotides 51 to 1000 of the PEP4 ORF (SEQ ID NO: 58) was prepared by PCR using primers 40 and 41 (SEQ ID NOs: 59 and 60) and genomic DNA of the *Pichia angsta* NCYC495 strain as the template. The resulting gene fragment was treated with SpeI and inserted into the SpeI site of pUC-1 to prepare pUC-PEP4.

The zeocin tolerant gene fragment prepared in Example 10 was inserted into the ScaI site in the PEP4 gene of pUC-PEP4 to prepare pUC-Δpep4. pUC-Δpep4 was treated with SpeI to construct a gene for PEP4 gene disruption comprising the zeocin tolerant gene inserted into the ScaI site of the sequence comprising nucleotides 51 to 1400 of the PEP4 gene.

The resulting vector for PEP4 gene disruption was used to transform the Fab antibody-expressing strain described in Example 2 and the Fab antibody-expressing strains with disruption of the VPS (VPS8, VPS10, and VPS15) genes described in Examples 3 to 5, and colonies were selected on the YNB plate containing zeocin at 0.1 g/l. PCR was carried out to confirm that the vector for gene disruption had been inserted into the PEP4 gene, and the Fab antibody-expressing strain with disruption of the PEP4 gene and the Fab antibody-expressing strain with double disruption of the PEP4 and VPS genes were obtained.

Comparative Example 2

YPS1 Gene Disruption

A fragment having the SpeI sites in sites upstream and downstream of a sequence of nucleotides 501 to 1700 of the YPS1 ORF (SEQ ID NO: 61) was prepared by PCR using primers 42 and 43 (SEQ ID NOs: 62 and 63) and genomic DNA of the *Pichia angsta* NCYC495 strain as the template. The resulting gene fragment was treated with SpeI and inserted into the SpeI site of pUC-1 to prepare pUC-YPS1.

The zeocin tolerant gene fragment prepared in Example 10 was inserted into the EcoRV site in the YPS1 gene of pUC-YPS1 to prepare pUC-Δyps1. pUC-Δyps1 was treated with SpeI to construct a vector for YPS1 gene disruption comprising the zeocin tolerant gene inserted into the EcoRV site of the sequence comprising nucleotides 501 to 1700 of the YPS1 gene.

The resulting vector for YPS1 gene disruption was used to transform the Fab antibody-expressing strain described in Example 2 and the Fab antibody-expressing strain with disruption of the VPS (VPS10) gene described in Example 4, and colonies were selected on the YNB plate containing zeocin at 0.1 g/l. PCR was carried out to confirm that the vector for gene disruption had been inserted into the YPS1 gene, and the Fab antibody-expressing strain with disruption of the YPS1 gene and the Fab antibody-expressing strain with double disruption of the YPS1 and VPS genes were obtained.

Example 11

Measurement of Amount of Fab Antibody Secreted

The VPS gene disruption strains and the double-disruption strains of the VPS and PRB1 genes obtained in Examples 3 to 10 and original strains (undisrupted strains) used for preparation of these gene disruption strains were subjected to sandwich ELISA (enzyme-linked immunosorbent assay) to analyze the amount of Fab antibodies secreted in the culture supernatant.

The culture supernatant was prepared in the manner described below. Specifically, Fab antibody-expressing strains were inoculated into 2 ml of BMGMY medium (1% Bacto Yeast Extract, 2% peptone, 1.34% yeast nitrogen base, 0.4 mg/l biotin, 100 mM potassium phosphate (pH 6.0), 1% glycerol, and 1% methanol), shake culture was performed at 30° C. for 72 hours, and the culture supernatant was prepared by centrifugation at 15,000 rpm and 4° C. for 1 minute.

Sandwich ELISA was performed in the manner described below. The anti-human IgG (Fab-specific) affinity isolated antigen specific antibody (SIGMA) diluted 5,000-fold with an immobilization buffer (a 0.1 N sodium bicarbonate solution; pH 9.6) was applied to an ELISA plate (MaxiSoap, Nunc) at 50 μl/well, and the resultant was subjected to incubation at 4° C. overnight. Thereafter, the solution was removed from the wells, Immunoblock (Dainippon Sumitomo Pharma Co., Ltd.) diluted 5-fold was added at 250 μl/well, and the resultant was allowed to stand at room temperature for 1 hour to block the wells.

The wells were washed three times with PBST (PBS (Takara Bio Inc.)+0.1% Tween 20), serial dilutions of the standard proteins (anti-human IgG Fab, Rockland) and the diluted culture supernatant were added at 50 μl/well, and the reaction was allowed to proceed at room temperature for 1 hour. The solution was removed from the wells, the wells were washed two times with PBST, a secondary antibody solution diluted 8,000-fold with a PBSTIB (PBST+1/50-diluted Immunoblock) solution (secondary antibody: Anti-human IgG (Fab-specific)-peroxidase conjugate antibody developed in goat affinity isolated antibody, SIGMA) was added at 50 μl/well, and the reaction was allowed to proceed at room temperature for 1 hour.

The solution was removed from the wells, the wells were washed four times with PBST, the SureBlue TMB 1-component microwell peroxidase substrate (KPL) was added at 100 μl/well, and the reaction solution was allowed to stand at room temperature for 20 minutes. The reaction was terminated with the addition of the TMB stop solution (KPL) at 100 μl/well, and the absorbance at 450 nm was then measured using a microplate reader (BenchMark Plus, Bio-Rad). The antibodies in the culture supernatant were quantified using the calibration curve for the standard protein. Thus, accumulation of antibodies secreted in the culture supernatant was confirmed.

The PEP4 gene disruption strain obtained in Comparative Example 1 and the YPS1 gene disruption strain obtained in Comparative Example 2 were inspected in the same manner concerning the amount of antibodies secreted in the culture supernatant.

The results are shown in Table 1 and Table 2 below.

TABLE 1

| Strain | Fab (mg/l) |
| --- | --- |
| Undisrupted strain | 4.6 |
| VPS8-disruption strain (Example 3) | 6.3 |
| VPS10-disruption strain (Example 4) | 6.2 |
| VPS15-disruption strain (Example 5) | 6.1 |
| VPS17-disruption strain (Example 6) | 5.6 |
| VPS21-disruption strain (Example 7) | 5.4 |
| VPS26-disruption strain (Example 8) | 5.2 |
| VPS45-disruption strain (Example 9) | 4.8 |

TABLE 2

| Strain | Fab (mg/l) |
| --- | --- |
| PRB1-disruption strain (Example 10) | 4.1 |
| PRB1/VPS8 double-disruption strain (Example 10) | 8.6 |
| PRB1/VPS10 double-disruption strain (Example 10) | 10.3 |
| PRB1/VPS15 double-disruption strain (Example 10) | 9.1 |
| PEP4-disruption strain (Comparative Example 1) | 4.8 |
| PEP4/VPS8 double-disruption strain (Comparative Example 1) | 4.6 |
| PEP4/VPS10 double-disruption strain (Comparative Example 1) | 4.5 |
| PEP4/VPS15 double-disruption strain (Comparative Example 1) | 4.0 |
| YPS1-disruption strain (Comparative Example 2) | 4.8 |
| YPS1/VPS10 double-disruption strain (Comparative Example 2) | 4.5 |

As shown in Table 1, the amount of Fab secretion increased as a result of disruption of the VPS gene. As shown in Table 2, the amount of Fab secretion further increased as a result of double-disruption of the VPS and PRB1 genes. In the case of double-disruption of the VPS and PEP4 genes or the VPS and YPS1 genes, however, the amount of Fab secretion did not increase any more.

INDUSTRIAL APPLICABILITY

The present invention can be used in the field of production of proteins used for treatment of diseases and, in particular, in relation to antibodies.

All publications, patents, and patent applications cited herein are incorporated herein by reference in their entirety.

The invention claimed is:

1. A method for producing a heterologous protein, characterized by comprising using methanol-assimilating yeast with simultaneous disruptions of the vacuolar protein sorting (VPS) gene and the vacuolar protease B (PRB1) gene as a host for secretory production of the heterologous protein, wherein the VPS gene is at least one gene selected from the group consisting of VPS8, and VPS15.

2. The method according to claim 1, wherein the methanol-assimilating yeast is a transformant of the genus *Pichia*.

3. The method according to claim 2, wherein the yeast of the genus *Pichia* is selected from the group consisting of *Pichia angsta*, *Pichia methanolica*, *Pichia minuta*, and *Pichia pastoris*.

4. The method according to claim 1, wherein the heterologous protein is a human or animal therapeutic protein.

5. The method according to claim 1, wherein the heterologous protein is an antibody or antibody fragment.

* * * * *

SEQUENCE LISTING

<160> NUMBER OF SEQ ID NOS: 63

<210> SEQ ID NO 1
<211> LENGTH: 1510
<212> TYPE: DNA
<213> ORGANISM: Pichia angusta

<400> SEQUENCE: 1

| | | | | | |
|---|---|---|---|---|---|
| tcgacgcgga | gaacgatctc | ctcgagctgc | tcgcggatca | gcttgtggcc | cggtaatgga | 60 |
| accaggccga | cggcacgctc | cttgcggacc | acggtggctg | gcgagcccag | tttgtgaacg | 120 |
| aggtcgttta | gaacgtcctg | cgcaaagtcc | agtgtcagat | gaatgtcctc | ctcggaccaa | 180 |
| ttcagcatgt | tctcgagcag | ccatctgtct | ttggagtaga | agcgtaatct | ctgctcctcg | 240 |
| ttactgtacc | ggaagaggta | gtttgcctcg | ccgcccataa | tgaacaggtt | ctctttctgg | 300 |
| tggcctgtga | gcagcgggga | cgtctggacg | gcgtcgatga | ggcccttgag | gcgctcgtag | 360 |
| tacttgttcg | cgtcgctgta | gccggccgcg | gtgacgatac | ccacatagag | gtccttggcc | 420 |
| attagtttga | tgaggtgggg | caggatgggc | gactcggcat | cgaaattttt | gccgtcgtcg | 480 |
| tacagtgtga | tgtcaccatc | gaatgtaatg | agctgcagct | tgcgatctcg | gatggttttg | 540 |
| gaatggaaga | accgcgacat | ctccaacagc | tgggccgtgt | tgagaatgag | ccggacgtcg | 600 |
| ttgaacgagg | gggccacaag | ccggcgtttg | ctgatgcgc  | ggcgctcgtc | ctcgatgtag | 660 |
| aaggcctttt | ccagaggcag | tctcgtgaag | aagctgccaa | cgctcggaac | cagctgcacg | 720 |
| agccgagaca | attcggggt  | gccggctttg | gtcatttcaa | tgttgtcgtc | gatgaggagt | 780 |
| tcgaggtcgt | ggaagatttc | cgcgtagcgg | cgttttgcct | cagagtttac | catgaggtcg | 840 |
| tccactgcag | agatgccgtt | gctcttcacc | gcgtacagga | cgaacggcgt | ggccagcagg | 900 |
| cccttgatcc | attctatgag | gccatctcga | cggtgttcct | tgagtgcgta | ctccactctg | 960 |
| tagcgactgg | acatctcgag | actgggcttg | ctgtgctgga | tgcaccaatt | aattgttgcc | 1020 |
| gcatgcatcc | ttgcaccgca | agttttaaa  | acccactcgc | tttagccgtc | gcgtaaaact | 1080 |
| tgtgaatctg | gcaactgagg | gggttctgca | gccgcaaccg | aacttttcgc | ttcgaggacg | 1140 |
| cagctggatg | gtgtcatgtg | aggctctgtt | tgctggcgta | gcctacaacg | tgaccttgcc | 1200 |
| taaccggacg | gcgctaccca | ctgctgtctg | tgcctgctac | cagaaaatca | ccagagcagc | 1260 |
| agagggccga | tgtggcaact | ggtggggtgt | cggacaggct | gtttctccac | agtgcaaatg | 1320 |
| cgggtgaacc | ggccagaaag | taaattctta | tgctaccgtg | cagcgactcc | gacatccccca | 1380 |
| gtttttgccc | tacttgatca | cagatggggt | cagcgctgcc | gctaagtgta | cccaaccgtc | 1440 |
| cccacacggt | ccatctataa | atactgctgc | cagtgcacgg | tggtgacatc | aatctaaagt | 1500 |
| acaaaaacaa | | | | | | 1510 |

<210> SEQ ID NO 2
<211> LENGTH: 606
<212> TYPE: DNA
<213> ORGANISM: Pichia angusta

<400> SEQUENCE: 2

| | | | | | |
|---|---|---|---|---|---|
| gagacgtgga | aggacatacc | gcttttgaga | agcgtgtttg | aaaatagttc | tttttctggt | 60 |
| ttatatcgtt | tatgaagtga | tgagatgaaa | agctgaaata | gcgagtatag | gaaaatttaa | 120 |
| tgaaaattaa | attaaatatt | ttcttaggct | attagtcacc | ttcaaaatgc | cggccgcttc | 180 |
| taagaacgtt | gtcatgatcg | acaactacga | ctcgttacc  | tggaacctgt | acagtacct  | 240 |
| gtgtcaggag | ggagccaatg | tcgaggtttt | caggaacgat | cagatcacca | ttccggagat | 300 |

```
tgagcagctc aagccggacg ttgtggtgat atcccctggt cctggccatc aagaacaga      360 ctcgggaata tctcgcgacg tgatcagcca ttttaaaggc aagattcctg tctttggtgt      420
ctgtatgggc cagcagtgta tcttcgagga gtttggcgga gacgtcgagt atgcgggcga      480
gattgtccat ggaaaaacgt ccactgttaa gcacgacaac aagggaatgt tcaaaaacgt      540
tccgcaagat gttgctgtca ccagatacca ctcgctggcc ggaacgctca agtcgcttcc      600
ggactg                                                                 606
```

<210> SEQ ID NO 3
<211> LENGTH: 1340
<212> TYPE: DNA
<213> ORGANISM: Pichia angusta

<400> SEQUENCE: 3

```
gagtccctga gtacgtaagc ggtttggtaa tacgaaataa aaagacagga atgagtaagt       60
ggatggtttt tcaattttc cggtaccggc gcaaaatagt tgcatcattt tgcaatcatg      120
agtaagaaca ttgtgcttct ccctggtgat cacgtgggcc ccgaggttgt tgcggaggcc      180
gtcaaggttc tcgaggctgt ctcgtcggca atcggcgtta agttcaactt ttccaagcac      240
ctgatcggcg gtgcctcgat cgatgcttat ggggtgccat tgtccgacga ggccctcgaa      300
gccgccaaga aggctgacgc cgttttgctt ggagccgtcg gaggacctaa gtggggaacc      360
ggctccgtgc gtcctgagca gggtctgttg aagatcagaa aagagctcaa cttgtacgcg      420
aacctgcgtc catgcagttt tgcttccgac gctcttctga agctatctcc actgaaatca      480
gaaatcgtca agggcactga ctttgttgtt gtgcgtgagt tggttggtgg aatctacttt      540
ggtgaccgca aggaggatgc cggcgacgga gttgccagcg acactgagag ctattctgtt      600
ccagaggtgc agagaatcac gagaatggcg gccttttgg cgctgcagag cgacccaccg      660
ctcccactgt ggtcgctgga caaagccaac gtgcttgcat cctcgcgttt gtggcggaag      720
actgttgagg agaccatcaa gaacgagttc ccgcagctga cggtgcagca ccagctgatc      780
gactcggcag ccatgatttt ggtcaagtcg ccaacgaaac tcaacggtgt cattgtcacc      840
aacaacatgt ttggcgacat catcagtgac gaggccagtg tgattcctgg gtctctgggc      900
ctgctgcctt ctgcctcgtt ggcgtctctg ccagacacaa acaaggcgtt tggtctttac      960
gagccctgcc acggctcggc gccagatttg gcccggggca aggtcaatcc attggccaca     1020
attttgtctg ccgccatgat gctgaagctg tcgctggact tggtggatgc cggccgtgcg     1080
atcgagcagg ccgtcaagaa cgtcctggat gcaggtatca tgactgccga tttgggtgga     1140
agctcctcaa cacaggaagt tggtgatgct gttgcgcagg aggtggccaa gctactcaag     1200
aactaaataa gggagaaaaa aaagtaggat ctcgaataat tcctaaataa tcccaaaaat     1260
cctaaacacg cacgcctcac agatttatt ttttcgacg cgacgctcta ttgtttattt     1320
tttagctttt ccatgtcaac                                                 1340
```

<210> SEQ ID NO 4
<211> LENGTH: 290
<212> TYPE: DNA
<213> ORGANISM: Pichia angusta

<400> SEQUENCE: 4

```
gctatacaga gctttatatc accttactga acgctagagt agacccaatt cccggctcac       60 accacccctta catgcagagc taaccaataa ggtaattaat taacactata tagctcgtgg      120
```

```
tgaacactgg cccggagtag tcatacgtgt aggttttgg cgtgatgaaa atcaggtggc      180
gcacgacttt tcgtaaagtt cgggagggag tgctgcaaac ggcatataag gaccagtttt      240
tctcgcacat tatcaattgc tctttagtac aaagataata tagaaaccat                 290

<210> SEQ ID NO 5
<211> LENGTH: 255
<212> TYPE: DNA
<213> ORGANISM: Saccharomyces cerevisiae

<400> SEQUENCE: 5
atgagatttc cttcaatttt tactgcagtt ttattcgcag catcctccgc attagctgct       60
ccagtcaaca ctacaacaga agatgaaacg gcacaaattc cggctgaagc tgtcatcggt      120
tactcagatt tagaagggga tttcgatgtt gctgttttgc catttccaa cagcacaaat       180 aacggttat tgtttataaa tactactatt gccagcattg ctgctaaaga agaaggggta       240
tctctcgaga aaaga                                                       255

<210> SEQ ID NO 6
<211> LENGTH: 645
<212> TYPE: DNA
<213> ORGANISM: Homo sapiens

<400> SEQUENCE: 6
gacatccaga tgacccagtc tccatcctcc ctgtctgcat ctgtagggga cagagtcacc       60
atcacttgtc gggcaagtca gggcatcaga aattacttag cctggtatca gcaaaaacca      120
gggaaagccc ctaagctcct gatctatgct gcatccactt tgcaatcagg ggtcccatct      180
cggttcagtg gcagtggatc tgggacagat ttcactctca ccatcagcag cctacagcct      240
gaagatgttg caacttatta ctgtcaaagg tataaccgtg caccgtatac ttttggccag      300
gggaccaagg tggaaatcaa acgaactgtg gcggcgccat ctgtcttcat cttcccgcca      360
tctgatgagc agttgaaatc tggaactgcc tctgttgtgt gcctgctgaa taacttctat      420
cctcgagagg ccaaagtaca gtggaaggtg gataacgccc tccaatcggg taactcccag      480
gagagtgtca cagagcagga cagcaaggac agcacctaca gcctcagcag caccctgacg      540
ctgagcaaag cagattacga gaaacacaaa gtctacgcct gcgaagtcac ccatcagggc      600
ctgagctcgc ccgtcacaaa gagcttcaac aggggagagt gttag                      645

<210> SEQ ID NO 7
<211> LENGTH: 1356
<212> TYPE: DNA
<213> ORGANISM: Homo sapiens

<400> SEQUENCE: 7
gaggtgcagc tggtggagtc tgggggaggc ttggtacagc ccggcaggtc cctgagactc       60
tcctgtgcgg cctctggatt cacctttgat gattatgcca tgcactgggt ccggcaagct      120
ccagggaagg gcctggaatg ggtctcagct atcacttgga atagtggtca catagactat      180
gcggactctg tggagggccg attcaccatc tccagagaca acgccaagaa ctccctgtat      240
ctgcaaatga acagtctgag agctgaggat acggccgtat attactgtgc gaaagtctcg      300
taccttagca ccgcgtcctc ccttgactat tggggccaag gaccctggt caccgtctcg      360 agtgctagct tcaaggggcc catcggtctt ccccctggcac cctcctccaa gagcacctct      420
gggggcacag cggccctggg ctgcctggtc aaggactact cccccgaacc ggtgacggtg      480
tcgtggaact caggcgcccct gaccagcggc gtgcacacct tcccggctgt cctacagtcc      540
```

```
tcaggactct actccctcag cagcgtggtg accgtgccct ccagcagctt gggcacccag    600
acctacatct gcaacgtgaa tcacaagccc agcaacacca aggtggacaa gagagttgag    660
cccaaatctt gtgacaaaac tcacacatgc ccaccgtgcc cagcacctga actcctgggg    720
ggaccgtcag tcttcctctt ccccccaaaa cccaaggaca ccctcatgat ctcccggacc    780
cctgaggtca catgcgtggt ggtggacgtg agccacgaag accctgaggt caagttcaac    840
tggtacgtgg acggcgtgga ggtgcataat gccaagacaa agccgcggga ggagcagtac    900
aacagcacgt accgtgtggt cagcgtcctc accgtcctgc accaggactg gctgaatggc    960
aaggagtaca agtgcaaggt ctccaacaaa gccctcccag cccccatcga aaaaccatc    1020
tccaaagcca agggcagccc cgagaaccag gtgtacaccc ctgcccccc atcccgggag    1080
gagatgacca agaaccaggt cagcctgacc tgcctggtca aaggcttcta tcccagcgac    1140
atcgccgtgg agtgggagag caatgggcag ccggagaaca actacaagac cacgcctccc    1200
gtgctggact ccgacggctc cttcttcctc tatagcaagc tcaccgtgga caagagcagg    1260
tggcagcagg ggaacgtctt ctcatgctcc gtgatgcatg aggctctgca caaccactac    1320
acgcagaaga gcctctccct gtctccgggt aaatga                              1356
```

<210> SEQ ID NO 8
<211> LENGTH: 795
<212> TYPE: DNA
<213> ORGANISM: Artificial Sequence
<220> FEATURE:
<223> OTHER INFORMATION: Synthetic

<400> SEQUENCE: 8

```
atgattgaac aagatggatt gcacgcaggt tctccggccg cttgggtgga gaggctattc     60
ggctatgact gggcacaaca gacaatcggc tgctctgatg ccgccgtgtt ccggctgtca    120
gcgcaggggc gcccggttct ttttgtcaag accgacctgt ccggtgccct gaatgaactg    180
caggacgagg cagcgcggct atcgtggctg gccacgacgg gcgttccttg cgcagctgtg    240
ctcgacgttg tcactgaagc gggaagggac tggctgctat tgggcgaagt gccggggcag    300
gatctcctgt catctcacct tgctcctgcc gagaaagtat ccatcatggc tgatgcaatg    360
cggcggctgc atacgcttga tccggctacc tgcccattcg accaccaagc gaaacatcgc    420
atcgagcgag cacgtactcg gatggaagcc ggtcttgtcg atcaggatga tctggacgaa    480
gagcatcagg ggctcgcgcc agccgaactg ttcgccaggc tcaaggcgcg catgcccgac    540
ggcgaggatc tcgtcgtgac ccatggcgat gcctgcttgc cgaatatcat ggtggaaaat    600
ggccgctttt ctggattcat cgactgtggc cggctgggtg tggcggaccg ctatcaggac    660
atagcgttgg ctacccgtga tattgctgaa gagcttggcg gcgaatgggc tgaccgcttc    720
ctcgtgcttt acggtatcgc cgctcccgat tcgcagcgca tcgccttcta tcgccttctt    780
gacgagttct tctga                                                     795
```

<210> SEQ ID NO 9
<211> LENGTH: 3629
<212> TYPE: DNA
<213> ORGANISM: Pichia angusta

<400> SEQUENCE: 9

```
atgccggcgc agttcaactt tgaccaccgg ttgcagtcgc gagtagccag aaatagggac     60
agcgttgctg ccggacacga attggagccg ctggagcggt cgcagtctcc gtcgttgtat    120
```

-continued

| | | | | |
|---|---|---|---|---|
| ggaagcgctt | ctgatcgcga | cgctatacag | ctgatcaccc | ttaaaaagat | cacgtcgcgg | 180 |
| ctgtttgaga | atccgcagca | gctcgaacaa | cagggcgagc | ccgtgtgcat | tgcggtttgc | 240 |
| gctaaatata | ttgcctttgg | aacatccaag | ggtcacgtgc | tggcgttcaa | ctacgaccag | 300 |
| tctctggagg | ctgccttctt | taccggagtg | cccatcacag | cgatctcgtt | ttcgctggac | 360 |
| tctaattcgc | ttgccacggg | ccacagaacc | ggccaagtga | gcatttacga | gctttcgaac | 420 |
| caggacaggc | cgtgccacag | ctttgactct | ctcagcagcc | cgatatccac | gctttcgttt | 480 |
| atcggcaagc | gccattcggc | tcttctgagc | accacggacg | acggcaggct | tgtgtaccat | 540 |
| cacgccacac | gcacgctgtt | tggattcagc | tgcagttcgc | gaacactggc | ggaaaatgtc | 600 |
| cttgcttccg | cacagctgtt | gatgggcccc | gtggcttacc | ctacagacac | tatgggcgtt | 660 |
| ctcgcgctga | tgtcgccgtc | cggactgacg | gttttatcga | cagagccggt | agtgcagact | 720 |
| catttcagag | tcgggaaacc | caaaattctc | gacgagaccg | acactttggg | ctgcgtccag | 780 |
| tggtttcctg | ctaccaaaga | gtttcccgcc | ctggcgtact | cgtggggcaa | cgtgctgacc | 840 |
| ttgatagacg | ttgtggcgga | gagatatgtc | gacgagcgca | aaagcgagtc | ggtcttgctc | 900 |
| cggtacgaga | acaaacgcag | gtacccgtgc | caggagccca | tagttgccat | acactggctg | 960 |
| aatgccaagg | ttctcgtggt | gctgaccgtt | tcacaacgcc | ttttctgtct | ttcgcgggaa | 1020 |
| aaactacagg | ttcttactga | acaggacgtg | atgaacaagc | acgtgaagca | tcggctcgca | 1080 |
| gactcgcagc | atcgcagctt | tgcagctacg | agtgcagttt | tccgaggaaa | actatttgtt | 1140 |
| ctgggaaaat | accaggcgtt | tttgggctcc | ccacgcaact | gggcagacga | gctgtttgag | 1200 |
| ttgctacagt | cgggccagta | cattaacgca | ctggagacgg | cacgcattca | gtacgatgga | 1260 |
| caatgcgatc | tggttttaat | cggattgcca | aaagatgacg | ccgaacgtca | tcagaaaatg | 1320 |
| cgccatcaca | tcatgcagat | gctcgaagcg | tcctccaaat | acatcttcac | cgaccagtcg | 1380 |
| gttcttgcga | tggaacctat | ggcacgaaaa | gacgttcttg | cgcaattcct | agccactgca | 1440 |
| ttcagagtct | gtgtcagtct | gaaaccggat | ccggcggttt | acgagcagct | gtttgagaga | 1500 |
| tacgtggcca | atgggcttga | ggatgtttat | tcggcattc | tggagaagtt | catccgcaaa | 1560 |
| caagaaatta | ctgtcctgcc | tcctgtcgtg | ctacgcaaaa | tggtggctcg | ctatgtctat | 1620 |
| gacggcagag | gccatactct | ggaggaaatg | atttgtttct | tggacttgaa | gcagttggat | 1680 |
| attgacctgg | ccatcactct | gtgtcgcgaa | caccacttga | acgactcgct | agcatacatc | 1740 |
| tggaacacca | tgctggacga | ctatatcacc | ccactcatag | acgctttgaa | agctttgaaa | 1800 |
| aagcatagca | acgagccgga | ataccgcgat | tccgactacg | tgtacgcata | catagcgtac | 1860 |
| attttgactg | gaagacagta | tccgaccgag | aagccgctta | actatagaac | gagcgagaca | 1920 |
| gcgagaaaga | atatttatta | tgtgcttttc | agcggagcag | ccatttcgtg | gccccgcggg | 1980 |
| actccaaaat | tcacatcgt | cgatgaagaa | aacgtagtcg | atgagcctgc | gttcccgtac | 2040 |
| cttttctgc | tgctcaagca | cgatggagct | cttttttcc | ggtgtctgaa | cgaagttttt | 2100 |
| gaggacactt | ttctcaacga | caacgaagtg | tttgggtttt | ccagcaactc | agacacttac | 2160 |
| gagctaaagg | tgagccgcca | atacattctc | gacgtcctga | tgggcatatt | tggcgagaac | 2220 |
| gactttggca | gcaagtacca | gacgtatttg | gctgttttca | ttgcccggaa | ctatcccaaa | 2280 |
| tacatgcagt | tcattcgact | ctccaattct | ttgctggagg | tggtaattcg | cgatctctgt | 2340 |
| gcgtatcccg | ttcctgaact | caaggaggaa | tgcgaattga | gcctgcagag | cctgcttttct | 2400 |
| gtgcacaagc | ccagcacgtc | cttggtacca | atgctggagt | ctgccggggtt | ttacaacgca | 2460 |
| ctaatgagca | tttatcaatc | tgagcagcgt | gcgctcaagc | tgctggagct | ttggattgag | 2520 |

```
cagaaaaaca ggccaaaggc cacggagatc atagaacgct gtttcagact cgtcagaaac    2580
aatactggcg aaaggctcga cgtggagcag tttctggaac gccatttctc cgagttttgc    2640
gccgaccctg ccgctgcagc caaagtgttc tccgagcact gtcaaaagct caactccaag    2700
gccctcgagc tgtctcagcc gcagaaatac gaatatctga gagcagtgtt cgatatccgc    2760
tctcagactg gactcgaagt atcttcggag atggaagttg cctacgcaga gtgtctgctt    2820
gagtacgagc ctgccagtct caagcagttt gtgctaggtt gcaagacgga cgagaaattg    2880
atgcattttc tgagagaaaa tcagcagttc gagacgattg tcgaaatcca ccgcagagca    2940
aacgagacca acaggccgt ggaggatatc atccaagcct tgacctactg cgccacacac    3000
ctcaaaaagg cagacaacag cgacgtcctc tggaggtatt tgtatctggg ctttgacgtc    3060
attagcgaat cgcggctcac tccagacgtg tcgcaggatc tccagccaga cgagagacta    3120
tacctgcggc ttgtggagac tgcggttgga ttttttgtgg cggccgaagg gccgttactg    3180
gacagtttca gcggctggt ccaggacgca ttcactacgc taattaacat caaaagagac    3240
cactcagact cgttttctcg catcttcaac gcgttcctga cgcgctcttc tgtccagctg    3300
acgacgctac aagaggtgcg gcccgtgctg gacgagatat ttcaggccta ctctcaccag    3360
gaggtgatct acaaaatcat cttgcggctg gtgaacaacg acattttcca ggaattgatg    3420
gtgctacagg cgaaaagaga atcaggctgg tcgctcgcca acctggagtg cgaggtgtgc    3480
ggaaagccga tctgggggtc gaaggtgagc gcccaggtgt tgatgagtg caggagtac    3540 cgtgtgcagg gcgtcgtgcg cgcgccgatc gacgcaaata tcatggtgtt ccaatgtcgt    3600
cacggttatc atacaagatg cctacataa                                     3629
```

<210> SEQ ID NO 10
<211> LENGTH: 4539
<212> TYPE: DNA
<213> ORGANISM: Pichia angusta

<400> SEQUENCE: 10

```
atgaagtggt caacgttgtt gtttcccgtc ctggctcttg tgactcttgt aggggctgcg     60
gactggaagc ctgcagtgtc gagaaaagag ttcagcacag gccacgacct tacgtacttt    120
gacgattcgt ctgtggtgct tattatagag gacaacaacc tgtacatatc ggaagacaat    180
gccaaaaact ggaaaaaggt ggatctcaaa aattctgctg gcaagaggt caactttacg    240 agtgttcaca cggtggacta tgccaaagag ctgggatttg ctctttccac gtccagaacc    300
cagttctaca cccgcgatcg cgggaaaacc tggactcctt tgaggtcga tcacagtgcc    360 agccaattca gcttgggtca tgttgaggtc aactatgcca ccacgacta tgtccttttc    420 agtttcatgg actgtgcggc gaacgagcaa tttgtgtttg agtgcaaaaa acctggtttt    480
ttcagcaacg atgggctgaa aacgcctcct aaaaaagtcg attacgacgg tttggaccac    540 tgtatttcg ccaagagcaa caaagcgttt acggcaggac cggacgagaa gatttatgt    600 tccaaagtgg acggggtcca ttcgggtatc gagaaaaaag gcgggcttct gaccacaaac    660
gatttcttca agaccgtgtc gtctccgtct gtagagttcg acaggatgaa cctcgtgtcg    720
atccgggtgg tccagtcatt cattattgcc actgttctg ttgacaagta cactcctgat    780
gccgaaatca tgctgtttat ttccaaggac ggagaaacgt tcagacgggc ttattttgag    840
gaccagctca agtcgtggat gttcagaata ttgccctcca cgccgcagtc gctctacatt    900
gccattcaga gccagcgtca gccaaaaat gctgcactgg atgcagattt gtacaaatcg    960
```

```
gactcgtctg ggctgttctt tgacaagatc cacgagaatg tcctgacaaa cgggctagga    1020
ttgtcggaca tcacgatggt gcaggaagtg gagggtgtta ttttactgct gagccacgaa    1080
aacgcggacg aggataacgc gccgccgctg gcgaagtcca agatctcgat tgacgacgga    1140
aagacatggc actatctcag aaccatcgat gacgatgact gcggcgggga ttccgagtgc    1200
tcgctcaact tgatgtggac cacgatcaga aacacaaacg gcaactttgc tactggcccc    1260
actccaggga tcctcgttgg aataggaaac atcggtaagc acctgacatc tgacctcaat    1320
gatctcaata cgtacatttc cagagacaac ggtgtaacgt ggaagaaagt cgtcgagggg    1380
tctgcagtgt tcacttttgc cgacctcgga aacatcattg ttgccatccg gatcgacgtg    1440
tcgcatctgt tcgactcgcg gctggaccca agtactcttc caaacacgtt cctgtactct    1500
cttgaccaag gaaactcctg gcaagaggcg actttggcg atcatatact gccgctcgat    1560
gttttcacgt ctctggacgg cagcacgcag catgttcttg ttacgggaga ggattcctcg    1620 cttttccaaga ttttttctgta tgccatagac ttcactggag cgtttgaaag aacttgttct    1680
gaagacgatt ttgaggactg gtacgccaga atgcttccgg acagcgactc tccagtctgt    1740
gttctgggac acacggaaaa gttcagaaga cggaagcaaa acgcggactg ttttgtgaac    1800
catccgtacg aggacctcaa agttatcgaa gagccttgca agtgcacgat tgacgatact    1860
gagtgcacgt tcggcttcat caaaggcgag aacgatgtct gtgagccagt tctggaggtg    1920
ttagccgcga atcagtgcgc aaaccagaag ggtgcgatca aaattacaac gagacagatg    1980
ataccgggcg acacgtgtga tccaaaaggc ggctacaaaa tagaaaaaga cgacttcagt    2040
tttgactgcg agaaggattt gcagaacatg accgctcctg tgaaagtcac gcacattccg    2100
ctgggcgaaa gaatcgccga gtatttctat ctcacctacg actcagacgg tcttccggac    2160
gagacacttt ttgtgctcac cgaaaacaag gttctataca tctcgtttga cggaggctct    2220
tcgtttggca agttcctgag cggccagcac attgtcacgg gcgtttacag caacccttac    2280
aaagcagacc acgtctacat tctgaccgac gccgatgcgc tctttttctc gcctgacaga    2340
ggagtctctg tctacgagcg cactctgccg gtcaggggcc acgatttcga gaagctctcg    2400
ctgaccttca ataagcacaa tgcctcgag tttattgtgc gtgccgaacg gagttgtggg    2460
aatctgtttt ccagcaactg tgtggtggag acgtatcaca cccaaaacta cggcgaatcg    2520
ttcgagcgtc tggtggccaa cgccaacacg tgcaactatg ccggctcgct gttcaatgac    2580
aaggagtacg ctgtgaacga gacactgatt gtatgcgacc agttcaccga cgaccgccag    2640
gctttgcggt taatctccag cacagactac ttccaaaagg agagcaaaac gctctttgac    2700
agaatcattg ggtttgcgca gacaggcaaa ttcatggtgg ttgcacggct ggacgacgac    2760
aactcgctaa ctgcgtttgt ttctgccgac ggcaagactt tgccgaggc aatgttcccc    2820 aaagacatca tggtcaccag acagacacg tacacgattt tggacgtgaa ctccgaccag    2880
attttcctgc acgtgaccac gcactcggcc tcgcggcacg agtttggtgc gctattgaaa    2940
tcgaattaca cggcacgca gtatgtgcag tcactgtccc atgtgaaccg caacgggttt    3000
gcatttgtgg actttgagag cgtgcagagt ttggagggaa tagccacggt caacgttgtg    3060
gccaactacg atgacgtggt gcgcaatggc gacgagaaga ctctcaagac catgatcacc    3120
tacaatgacg gcgccgagtg ggactatctg gttcctccgc ctgtggattc tgacggcaaa    3180
aagtacaagt gcagcggcaa gaaggagtgc acgctgaatc tgcactcgtt taccgaaaga    3240
aacgaccctg cgagagacac gtattcgtcg gcctcggccg tggggctgct ttttggagtt    3300
ggaaatgtcg gcacggcact gctgccgtac agttcaccgg aaacggcaac tttcttctcg    3360
```

```
aacgacgcgg gagcaacatg gaaagaagtc aagaagggca attacatgtg ggagtttggc   3420
gaccagggca cgattcttgt gctggtgaag cagggactca caaacaccgt gtcgtactct   3480
cttgacgaag gcgagacttg gcaggattac gagtttgcag agtctccaag gaacgtctgg   3540
gacattgcga cggttccctc cgacacggcc cgcaagttca tcctgctggc caaggacgac   3600
agaggccgcg acgagatata cagtctgaac tttgccgccc tccagaagcg acaatgcgag   3660
ctaacggtga cgaccagaa cgagctgacc gattttcgg actacgagta ctggtcgcct   3720
aaacacccgc accagtcgga caactgtctg tttggccacg aggccaggta tccaaggcgc   3780
aaggcgtcac aatcggactg ttttgtcggt gctgcgccgc tgaacaagct gtacaagaag   3840
accaagaact gcaaatgcac gcgtcacgac tttgagtgcg actacaattt tgtgctggcc   3900
gccgacggca cgtgccagct gatcaagggt ctgaagccag cagacccaac agaatattgc   3960
cagctggacg agaaccaggt cgagtactgg gagccgaccg gataccgaaa aattccaatg   4020
agcacctgcg agcagggact agagctggac aaatggattt ctcatccatg tccgggcaag   4080
aaagagcagt acaaggacaa atacggcgcg ggattgcacg gcgcgggcct tttctgggtg   4140
attttcgcac cgattgccgc gtttgttggg gctgccatct ttgtttacga cagaggaatc   4200
cgtcgtaatg gaggttttc gaggtttgga gagatccgtc ttgacgagga cgaagaactg   4260
cacctgatag aggagacgcc tgtggaccgc gccgtgaaca aggtcgtgag gggcggtttt   4320
gtgtttgtga gcgcggtggt ggcattacaa caccggctct cgagtttcct gaaaaacggc   4380
gttttttcgc gcttcagacg gggcggcctc gacaactacg aacagtttgc gtcgttcaac   4440
gaccgcatta tcgacgacga ggacgagtcg ctgttcgacg tgaacgccaa cgacgacgac   4500
gcgcgtgaga tcgacgactt ccttgacgag gagcaataa                          4539
```

<210> SEQ ID NO 11
<211> LENGTH: 4185
<212> TYPE: DNA
<213> ORGANISM: Pichia angusta

<400> SEQUENCE: 11

```
atgggtgccc agttgtcgct tctgtcgccc acagcacaga caattgccgt ttccgcctac     60
atagactatc tcagtgatgt tcagtacagc aaaccgttaa gctcgactcg atttctgaag    120
accatcaaat gtcttgacaa agaagggggcc gttgttgtca agctactcat aaagcccagc    180
accgagctaa atctcgaggc ctgggtgcgc gagctggaaa agctgagggt cgacttgttg    240
gaattaccta acgtcttacc ctttgagaaa ataatagact cccagagagc aggatacctg    300
attcgccctt atattcgcta caatctctac gaccggataa gtatccgtcc attttggag    360 ccgatcgagc gcaaatggat tgtgtaccag cttcttgttg gactttctcg catgcatcag    420
aaaaacgtgt accatggcga tctgaaaaca gaaaatgtgc tgatgacgtc ctggaactgg    480
tgtctgatca gtgactttgc tgtgttcaag cctgtgtatc tgccagagaa caacccttcg    540
cagttttcgt tctactttga taccagccag cgccacacgt gccatgttgc tcccgagcgg    600
tttcttgctt cagacaaaga agtcgacgag catccggacg ccaaactgac ctggcaaatg    660
gacattttct cgctggggtg tgccattgcc gagatctatc tcgagggtct ctcaattttc    720
acgcttgcgc agctattcaa gtacaaaaaa ggtgaatacc agccgaactt ggacacgata    780
gacgacataa acgtgcgcag actgatccag agcatgattg ctctagaccc ccggcagcgg    840
ctctctgcgc aggattgtct gacccagttt cgccgctctg tgtttcccga ccattttac    900
```

```
acgtttctgc atccatatat gaggaaactc agcgacatta cagaggtaag cgatccgttt    960
cgcagctgcg acatgcgcat tgcccgcgtt tacaacgatt tcgataaaat ctcgctttat   1020
ttagggttca agcaccaata cgacgacgac aagaaacaag tcacagatac aatgattcct   1080
gttcgtttgc agctgcccgg catgaacgac catgtgccca aaccgacaaa tgaggttttc   1140
aaggcctcga acgactgcgc gtctttaatt ttgctgtcct tggtgctgca tagtgtgcga   1200
aactcgacgc attcgtcgtt cagagtgcag gcctgcgata tcattctctc ctttgcagaa   1260
cagctccacg acgaggccaa gctggacagg tgtctgccgt atctaatgta catgctggac   1320
gatccgagcg aggacgtaca gagtgctgct ctgcggtgtt tggctcagct tctgaccatg   1380
gtggacgtga ttacacccgt caacgcatac atcttcccgg aatacgttct ccccaagcta   1440
cagcagtttc tcaagcgcac gtatcaggat accacgcagc cggaggctgg ccgatatctg   1500
cggtctgtgt ttgcgggctg tctgccctac ttggcgcgga ccgcgcgccg gttctacgaa   1560
atggccacgc ttttcagcgt gcaaccgcag cacgcggcgt ccgacgagtt tgcgatcgag   1620
aacgacctgc agctggaaaa atcattcaag aacatggtgg tggagtttga gtcactcgtg   1680
gtgcagatcc tcaccgacca ggactcgttt gtgcgtatct cgctgctgaa aaatatttta   1740
cccttgctg cgttttttcgg caaagacagg accaacgaca tcattctgag ccatctcatc   1800
acatacctca atgataagaa ccccaacatc cggctcggtt ttgtcgccag catcgtgccc   1860
atctctgttt tcgtcggcat tgtcagtttg gagcagtaca ttctgccgct cttagtgcaa   1920
tcgctgaacg acgccgacga gctggtcgtc atcggtgtta tcaagacttt cacggagctc   1980
tgcaaacttg gactcgtgcg caaagtccac tactgggacc ttgtcaagct cacgatccgt   2040
ctgctgctgc tcccaaacga gaccatcaga caggcggtac tcgatcttgt tgtggccgtc   2100
ggttctagtc tgtcacttgc agacctctac tgcatgctct acccgatcat caggccattt   2160
ttccaggacg aattgaccga gttttcgtgg gagtcgctct atatcagtgc ccagcagccg   2220
atttcgcttg ccgtgtacac actggcgcaa gcgtggtccc tgaaacagga ccagtcgctg   2280
ttttggcagc gtgtagaggc gtcgcaccgc cgcggagacc tgttcaacac gtctggcatc   2340
gcattttttgc gcaaaaacgt ggcccagagt tcgctgcatc gcttccatgg cgtcgacgac   2400
atgacggtgg tggccaacaa tgaggtgcca ctgagccaga gcgatctgca gcacgtcgag   2460
cggctcaagt ccgtggggat ggccgactcg gagctctgga agtggcgac gctgcgctcc   2520
tacatctaca aaatcgcacg caccaatagc cagcaaatga tttctgccga tgtatccaag   2580
cccaatgtgc tcccacgtac cgtgttcttc gatgtcttgc accgctcgga ggtggttccg   2640
agcgaggacc ctgcgtcagg agccctgaac ggctctgcgg cgtcgtctgc tcccagaaag   2700
gcgcctgctc tgctgtacgg tactgccgct aaagcagacc cgctcacatt caccagcagc   2760
cgcgcagtcg gcggagaaac aacgtcgctg ccgccgtcga cgcctgtttc tgccgaggag   2820
tcgaccagcg tccagaaaat caccaccaaa attaaacaca gctactccgg aacaaacccg   2880
tacattctca aattcttggg cagcatgtcc ttcgagccga ctttggacga ctataacgag   2940
ttcggcgggc ctgccgcggc atacgaacca cccgaaactc gcgagaaatc acaggtgtct   3000
ggaacattga tttcccggct ggtggagcac aaggcggcta tcaccggcct cgaagtttct   3060
ccggatcata agttttttcat ctcgagcgac gagtccggcg agctcaagct gtgggattct   3120
gcgcggctcg agatgaacgt caccgggtcg tcgacgctgg ccgttaacct ggaatcaccg   3180
attgtggcta tcaaatttat gccaaataga tactgtctcg cggtagccac caaggacggc   3240
tacatcaaga ttttccgact tgagtttgca aacacgcaca gaagacactc ctccgccaaa   3300
```

-continued

```
acgagcctca tcagacacta caagctggac aaaaccgaca ggtatgcact gcagctgggg   3360
ttcttctggc gggctgaaaa accgcttctg gtggccacca cgccaacatc caagcttttt   3420
ggccttgatg tacgcaccat gaagcctgtc ttttcggtgc agtgcaacct atcgcacggg   3480
ataccgaccg cgctagcggt ggacgagtcg cagggttggg ctgttgtcgg tacgtcaaag   3540
ggtatcttgg acctgtggga cttgaacttt gagatctcac tgaagagcgc aaaattccgc   3600
ggatcgagct tcccgatcca ccgcatcgag actttgccgc cagagtactc gccgaacggc   3660
agaaagtcca gatacatagc cgtgattggc ggctctggcg acgcagacgt gactgtctgg   3720
gacgtggcac gcctgcagcc ccgacaggtt ttctgctgct ccagcgtgtc ctccacgatc   3780
gaaacgtaca tcgtgaccga gctgggcaac gagaacgatt cgctggacga ccagctggcg   3840
cagctcgagc tctctgatga gctaatcacc gccgacaaaa gttgcacagc cttgaaatgt   3900
gccggcgggg tgttggtgag cgctgctcca cacaaccagc tgactgtgtg ggaccttggc   3960
gagcccgagc gctcgtgttt ggtggggaac gccgcggcgg cgtcgtttgt ggcgacgcag   4020
atcaactcga atctcatgtt tgtgagcgag cgacgcacag gccagaaacg cacggccgca   4080
gcggtcggcc accgcgaccg ggtgctgcac attgcgtggg tgtgtctgcc gtacgacatg   4140
ctcgtcagtg gcgaccgcag cggcaccatc aacgtgtata ggtga              4185
```

<210> SEQ ID NO 12
<211> LENGTH: 1572
<212> TYPE: DNA
<213> ORGANISM: Pichia angusta

<400> SEQUENCE: 12

```
atgacgtctg ccgtgcctta cgagcccgat gatttcgata taacccgtt tgccgagagc     60 agcgtgatta tacagtccca ggagcagcag actgctgacc cagtccagcc gacgactgcg    120
tcttcgtcgg acaaggacat agaagcgcag cccaaagaac aagactctcc tttccatcca    180
aaacccaccg acaacgattt aaaaagatac ttgcccgagc gactcaacag aaactcgttt    240
gagctgagta tcaaggtagt ggaaatcggc aataacggtg ccgaaatggc caagaacccg    300
gtctttgttc tgaatgcctc ggtgaagaat atcccagggt tcagaaaatc tgtctacaaa    360
gacgtgagaa gatcctacag agaactcgag gcaatctatc ggtatttgat atacaacaac    420
attgaggtgt ttgtgcctgc cctgcctact attcctgccc tctacaacgc cgggtcgccc    480
gagtttgtgg ccacgctgca gtcttcggtg cagcaatggc ttaatagagt ttgcagcaac    540
ccaattttga tccgcaacca ggagtttgtg ctgtttttgg accagaacga cttcagttac    600
acgccctcga aaaccaaacc caacaacagc tctgtgatgg ccaccggcct gaaacggcgc    660
acattgaagc aattccagcc gccatacgat gcatctcacg aattggcagc ttataggcca    720
atgatcaaga gcgtttatgt gagcgcgcag agactggttg agaaactgga caagttgttg    780
agactacaga atcgtcctg gctcgtgacc tctgatttct acaacaagct cgcagggctc    840
caagctcttg aggaaagccc cgaaatggcc aaaatgtggg ccaagctgaa caaagtgatg    900
caactgtaca acgagatgga tctggtgcaa ggtgtgagct tgacagcgaa tctgaccgaa    960
ttctttcaat tgctgacaga cgactgctat aacatcaaag agtctctgac aaaccgccat   1020
ctgctgatgc gcgagcttct aaatgcagag gaaaccacta aaaaacgcca ttccataatt   1080
gcaagactga aaaccaaatc catcatcgac ccagtgaaag tcgacgaggc catccgcgcc   1140
ttggaaatgg ccagcaatta cgagaaggac ctaaggtacc aagtgaaaag aactacgtac   1200
```

```
gaaatgctga tcgaggccga ggactttttg gtgtacttga ctgatctgac caaaaaaact   1260
ttcaagactc ttgctcagca acaaatacaa caacagcgca agaaactcca tcttctcaac   1320
atcaacaagc tgattcaccc aaccgagtct cttagtagac ttggccgcga gagcatgctg   1380
caaagcgtga ggagcgagcc tgcctcaaaa gactcttcag acccatggaa ctcgcggcca   1440
aaaaagaagt ttgaaacaga attgagcgac ccattgacgg cagagtcatc gctgggaaat   1500
gaacctgccg accagctcgc ccacctggac gccaggagcg ctgccagctt gctggccaac   1560
tcgaccttct ag                                                       1572

<210> SEQ ID NO 13
<211> LENGTH: 636
<212> TYPE: DNA
<213> ORGANISM: Pichia angusta

<400> SEQUENCE: 13
atgtccaaac aaacgtctgt taaacttgtg ctgctaggcg aggcagccgt cggaaagtcc     60
tcgctggtgc tgcgattcgt gtcgaacgac ttccaggaaa acaaagagcc caccatcggc    120
gctgcgttcc tcacccagcg gtgcactatt ggaacaaaga ccatcaagtt cgagatatgg    180
gataccgctg ccaggagag atttgccaat ctggccccgc tatactacag aaacgcgcaa    240
gcagcactgg ttgtgtacga tgttacaaag ccagcaagct tcatcaaagc caggcattgg    300
gttaaagagt tgcacgaaca ggcctcaaag aatatcgtga ttgctctggt cggcaacaag    360
tacgacctgg tggtggaccc agagacgggc gaggagatcg agggccgcag aagcgtctct    420
gtcgaagagg gcaaagctct ggccgacgag aaggattgtg tgttttttga daccagtgcc    480
aagaccgctt tcaacgtcaa cgaggtgttc acagcaattg aaaacagat tccggaagag    540 acgtcaaaac cccaggacga gccctcttcg gtcggaagaa tagacctcaa cgcccctgtc    600
gacgagtccg gaggggccgg caactgcgct tgctga                             636

<210> SEQ ID NO 14
<211> LENGTH: 912
<212> TYPE: DNA
<213> ORGANISM: Pichia angusta

<400> SEQUENCE: 14
atgtctttca tattcaagtc gccgctggac atacagcttc gtcttgacgg agaggactcg     60
cgtgagacag tggaacagaa gggcgtcaag ggacgcaagg aaaagctccc gttgtacaag    120
gacggcgaga ccgttaaggg ccaggtgacc ataagaacta gagacaacaa gagggtggag    180
cacacaggaa tcaagattca gcttttaggc acgatagaga ccaacaatga tggcctggtg    240
accgacaatt tcctgtcaat ggcgcacgag cttgccagtc ccggggaact gaggcatcca    300
gagacgtttc cgttcgagtt cagaaacgtc gagaaacagt acgaaagtta ccgcggcatc    360
aatgtacgtt tgcgatacta tctcaaagtg actgtttcgc gcaagtcagc agatgtgatc    420
agagagaaag agctttgggt gtaccagtac caggaccccg agcgcagat tccgagagc    480 gtggtgccca cgagctcggt gaaaatggat gtcggaattg aggattgttt gcatattgag    540
ttcgagtact ccaagaataa atactccctg aaagacgtga ttgtgggaag aatatacttt    600
ctgctggtgc ggctcaaaat caagcacatg gagctctcac tcatacgaag agagtcgtgt    660
ggagcgcctc caaaccagat gaatgagagc gagaccgttg tcaagtttga aattatggat    720
ggggcccctg tcagaggaga gacgattcca ataagattgt ccttggtgg attcgaccta    780 acgccgacgt acagagacgt caacaagaag ttctccacga gaacattcct cagcctggtc    840
```

```
ctgatagacg aggatgctcg tcggtacttt aaacagagcg aaatcatact gtatagggaa    900
aagaacgaat ag                                                        912
```

<210> SEQ ID NO 15
<211> LENGTH: 1728
<212> TYPE: DNA
<213> ORGANISM: Pichia angusta

<400> SEQUENCE: 15

```
atggacctct acgccgttgc ccagcactat ttggaccgca tactggaaaa ggactctagc     60
gacaatatcc gcgttctgct gttagacaaa accacgtctg cggtgatttc aatggtcacg    120
acacagtcgg aattgctcaa gaaagacgtg tttctcgtgg acaagctcga caacttccag    180
agagacagtc tgcgcaacct gtcgtgtatc tgttttctcg agcccagtat ggagacgatt    240
gccaatctgt cgcgcgaaat tgccaaccca aactaccaga atacgacct  tttctttaac    300 aattcggtgt cgaactccaa attgaacgc  tggcagagt  cggacgacct ggagacaatt    360
tccaaagtgg tggagatttt catggactac ctcgttgtga acaaggcgtt ttttgtcgtg    420
cccaacgtcg tctcgccgta tggcccgctc gtccgcgact cctgggacca ggcggcgttc    480
gaccagtctc ttcagagcgt catgtcgctg ctgctctcgc tcaagtacaa gcctgtcatt    540
cgctacgaaa cgaactcgaa aatgtgcgcc aagctcgcca acgcggtgaa cttcgaaatc    600
aactccaacc agatgctttt tggccagctg ccgttaagag actcgccgcc gtcgctgctt    660
atcttggacc gcaaaaacga ccccatcacc ccgttgctct cccctggac  gtaccaggcg    720 atgatccatg agctgctggg aatccacaac aacaccgtca acatgtcgcg cgtccacaac    780
atctcggaag agctcaagga ggtggtggtc aacgaacaaa cagaccagtt ctacaaagag    840
tctatgtacc ttaatttcgg agacctctca gagagtctca agagatttat cgagacatac    900
aaggcgaaaa cgaaaaccag ttccaacatc agcaccatca cagacatgaa gttttttcctg    960 gaaaactacc ccgagttcaa gaaaacgtcc atcaatttgt cgaaacacat gctgctctcc   1020
accgagatcg acaagaaaat caacgagctg cggctttggg aggtgggcga gctgcagcag   1080
tcgctcgcca caaacgataa cagtagcggc gatcttgcag aactcgagga cttgctattt   1140
gacagaaaat tgcagaacgg cgcccctgcg gctccgttgt ccgaagacac caaactaaag   1200
ctcctggcag tgtacgcgtt gcgatacgaa tcacatccgt ccaaccagct ctccagactg   1260
actagacagc tgcaccagct cgggttcccg agccacaagc tggacttgat taaacacctg   1320
ctgcagacca gcggcacgtc acagcgcctg cacgacgacg cgagtcgat  ctttgagaaa   1380 gtgtccaact cgacgatggg aggcaccgtc aacggcatca gcttcaagaa caacacggac   1440
ggaaacgtgt acatgcagca cagtccgcgg ctcaaacagg tgctgatgaa gttgttcaaa   1500
aacaagctca acaccaagaa ctatgcgctg ctcaagccca acggcttgga ggcgtacgcg   1560
ggcaacgaca agatcccgga ccaggaactc gttattttca ttgtgggcgg cgtgacgtat   1620
gaggaggccc ggctagttgc cgagctcaac cagctcaacc ccggcctgaa aattgtgatt   1680
ggcggaacac acatactaga ctcagacacg tttatagggc tgaaatga               1728
```

<210> SEQ ID NO 16
<211> LENGTH: 50
<212> TYPE: DNA
<213> ORGANISM: Artificial Sequence
<220> FEATURE:
<223> OTHER INFORMATION: Synthetic

<400> SEQUENCE: 16
aagcttgcgg ccgcggatcc actagtcaat tgagatcttc tagagaattc                    50

<210> SEQ ID NO 17
<211> LENGTH: 30
<212> TYPE: DNA
<213> ORGANISM: Artificial Sequence
<220> FEATURE:
<223> OTHER INFORMATION: Synthetic

<400> SEQUENCE: 17
ataaaagctt gagtccctga gtacgtaagc                                          30

<210> SEQ ID NO 18
<211> LENGTH: 30
<212> TYPE: DNA
<213> ORGANISM: Artificial Sequence
<220> FEATURE:
<223> OTHER INFORMATION: Synthetic

<400> SEQUENCE: 18
tataaagctt gttgacatgg aaaagctaaa                                          30

<210> SEQ ID NO 19
<211> LENGTH: 30
<212> TYPE: DNA
<213> ORGANISM: Artificial Sequence
<220> FEATURE:
<223> OTHER INFORMATION: Synthetic

<400> SEQUENCE: 19
ataaggatcc tcgacgcgga gaacgatctc                                          30

<210> SEQ ID NO 20
<211> LENGTH: 30
<212> TYPE: DNA
<213> ORGANISM: Artificial Sequence
<220> FEATURE:
<223> OTHER INFORMATION: Synthetic

<400> SEQUENCE: 20
tataggatcc ttgtttttgt actttagatt                                          30

<210> SEQ ID NO 21
<211> LENGTH: 30
<212> TYPE: DNA
<213> ORGANISM: Artificial Sequence
<220> FEATURE:
<223> OTHER INFORMATION: Synthetic

<400> SEQUENCE: 21
ataacaattg tcgacgcgga gaacgatctc                                          30

<210> SEQ ID NO 22
<211> LENGTH: 30
<212> TYPE: DNA
<213> ORGANISM: Artificial Sequence
<220> FEATURE:
<223> OTHER INFORMATION: Synthetic

<400> SEQUENCE: 22
tatacaattg ttgtttttgt actttagatt                                          30

<210> SEQ ID NO 23
<211> LENGTH: 30

```
<212> TYPE: DNA
<213> ORGANISM: Artificial Sequence
<220> FEATURE:
<223> OTHER INFORMATION: Synthetic

<400> SEQUENCE: 23
ataatctaga gagacgtgga aggacatacc                                          30

<210> SEQ ID NO 24
<211> LENGTH: 30
<212> TYPE: DNA
<213> ORGANISM: Artificial Sequence
<220> FEATURE:
<223> OTHER INFORMATION: Synthetic

<400> SEQUENCE: 24
tatatctaga cagtccggaa gcgacttgag                                          30

<210> SEQ ID NO 25
<211> LENGTH: 30
<212> TYPE: DNA
<213> ORGANISM: Artificial Sequence
<220> FEATURE:
<223> OTHER INFORMATION: Synthetic

<400> SEQUENCE: 25
ataaactagt atgagatttc cttcaatttt                                          30

<210> SEQ ID NO 26
<211> LENGTH: 23
<212> TYPE: DNA
<213> ORGANISM: Artificial Sequence
<220> FEATURE:
<223> OTHER INFORMATION: Synthetic

<400> SEQUENCE: 26
tcttttctcg agagataccc ctt                                                 23

<210> SEQ ID NO 27
<211> LENGTH: 40
<212> TYPE: DNA
<213> ORGANISM: Artificial Sequence
<220> FEATURE:
<223> OTHER INFORMATION: Synthetic

<400> SEQUENCE: 27
gggtatctct cgagaaaaga gacatccaga tgacccagtc                               40

<210> SEQ ID NO 28
<211> LENGTH: 30
<212> TYPE: DNA
<213> ORGANISM: Artificial Sequence
<220> FEATURE:
<223> OTHER INFORMATION: Synthetic

<400> SEQUENCE: 28
tataactagt ctaacactct cccctgttga                                          30

<210> SEQ ID NO 29
<211> LENGTH: 30
<212> TYPE: DNA
<213> ORGANISM: Artificial Sequence
<220> FEATURE:
<223> OTHER INFORMATION: Synthetic

<400> SEQUENCE: 29
```
ataaagatct atgagatttc cttcaatttt                                    30

<210> SEQ ID NO 30
<211> LENGTH: 40
<212> TYPE: DNA
<213> ORGANISM: Artificial Sequence
<220> FEATURE:
<223> OTHER INFORMATION: Synthetic

<400> SEQUENCE: 30
gggtatctct cgagaaaaga gaggtgcagc tggtggagtc                         40

<210> SEQ ID NO 31
<211> LENGTH: 30
<212> TYPE: DNA
<213> ORGANISM: Artificial Sequence
<220> FEATURE:
<223> OTHER INFORMATION: Synthetic

<400> SEQUENCE: 31
tataagatct ttaacaagat ttgggctcaa                                    30

<210> SEQ ID NO 32
<211> LENGTH: 30
<212> TYPE: DNA
<213> ORGANISM: Artificial Sequence
<220> FEATURE:
<223> OTHER INFORMATION: Synthetic

<400> SEQUENCE: 32
ataaactagt tttcacaacg cctttctgt                                     30

<210> SEQ ID NO 33
<211> LENGTH: 30
<212> TYPE: DNA
<213> ORGANISM: Artificial Sequence
<220> FEATURE:
<223> OTHER INFORMATION: Synthetic

<400> SEQUENCE: 33
tataactagt ttcaccagcc gcaagatgat                                    30

<210> SEQ ID NO 34
<211> LENGTH: 30
<212> TYPE: DNA
<213> ORGANISM: Artificial Sequence
<220> FEATURE:
<223> OTHER INFORMATION: Synthetic

<400> SEQUENCE: 34
ataaaagctt gctatacaga gctttatatc                                    30

<210> SEQ ID NO 35
<211> LENGTH: 40
<212> TYPE: DNA
<213> ORGANISM: Artificial Sequence
<220> FEATURE:
<223> OTHER INFORMATION: Synthetic

<400> SEQUENCE: 35
aatccatctt gttcaatcat atggtttcta tattatcttt                         40

<210> SEQ ID NO 36
<211> LENGTH: 20
<212> TYPE: DNA
<213> ORGANISM: Artificial Sequence

```
<220> FEATURE:
<223> OTHER INFORMATION: Synthetic

<400> SEQUENCE: 36
atgattgaac aagatggatt                                              20

<210> SEQ ID NO 37
<211> LENGTH: 30
<212> TYPE: DNA
<213> ORGANISM: Artificial Sequence
<220> FEATURE:
<223> OTHER INFORMATION: Synthetic

<400> SEQUENCE: 37
tataaagctt tcagaagaac tcgtcaagaa                                   30

<210> SEQ ID NO 38
<211> LENGTH: 30
<212> TYPE: DNA
<213> ORGANISM: Artificial Sequence
<220> FEATURE:
<223> OTHER INFORMATION: Synthetic

<400> SEQUENCE: 38
ataaactagt gtttggaggg aatagccacg                                   30

<210> SEQ ID NO 39
<211> LENGTH: 30
<212> TYPE: DNA
<213> ORGANISM: Artificial Sequence
<220> FEATURE:
<223> OTHER INFORMATION: Synthetic

<400> SEQUENCE: 39
tataactagt ttcacgtcga acagcgactc                                   30

<210> SEQ ID NO 40
<211> LENGTH: 30
<212> TYPE: DNA
<213> ORGANISM: Artificial Sequence
<220> FEATURE:
<223> OTHER INFORMATION: Synthetic

<400> SEQUENCE: 40
ataatgtaca gctatacaga gctttatatc                                   30

<210> SEQ ID NO 41
<211> LENGTH: 30
<212> TYPE: DNA
<213> ORGANISM: Artificial Sequence
<220> FEATURE:
<223> OTHER INFORMATION: artifcial

<400> SEQUENCE: 41
tatatgtaca tcagaagaac tcgtcaagaa                                   30

<210> SEQ ID NO 42
<211> LENGTH: 30
<212> TYPE: DNA
<213> ORGANISM: Artificial Sequence
<220> FEATURE:
<223> OTHER INFORMATION: Synthetic

<400> SEQUENCE: 42
ataaactagt tcaagcctgt gtatctgcca                                   30
```

<210> SEQ ID NO 43
<211> LENGTH: 30
<212> TYPE: DNA
<213> ORGANISM: Artificial Sequence
<220> FEATURE:
<223> OTHER INFORMATION: Synthetic

<400> SEQUENCE: 43
tataactagt cagactagaa ccgacggcca                                    30

<210> SEQ ID NO 44
<211> LENGTH: 30
<212> TYPE: DNA
<213> ORGANISM: Artificial Sequence
<220> FEATURE:
<223> OTHER INFORMATION: Synthetic

<400> SEQUENCE: 44
ataaactagt cagccgacga ctgcgtcttc                                    30

<210> SEQ ID NO 45
<211> LENGTH: 30
<212> TYPE: DNA
<213> ORGANISM: Artificial Sequence
<220> FEATURE:
<223> OTHER INFORMATION: Synthetic

<400> SEQUENCE: 45
tataactagt gtcggcaggt tcatttccca                                    30

<210> SEQ ID NO 46
<211> LENGTH: 30
<212> TYPE: DNA
<213> ORGANISM: Artificial Sequence
<220> FEATURE:
<223> OTHER INFORMATION: Synthetic

<400> SEQUENCE: 46
ataaactagt ctgctaggcg aggcagccgt                                    30

<210> SEQ ID NO 47
<211> LENGTH: 30
<212> TYPE: DNA
<213> ORGANISM: Artificial Sequence
<220> FEATURE:
<223> OTHER INFORMATION: Synthetic

<400> SEQUENCE: 47
tataactagt tcgtcgacag gggcgttgag                                    30

<210> SEQ ID NO 48
<211> LENGTH: 30
<212> TYPE: DNA
<213> ORGANISM: Artificial Sequence
<220> FEATURE:
<223> OTHER INFORMATION: Synthetic

<400> SEQUENCE: 48
ataaactagt atacagcttc gtcttgacgg                                    30

<210> SEQ ID NO 49
<211> LENGTH: 30
<212> TYPE: DNA
<213> ORGANISM: Artificial Sequence
<220> FEATURE:
<223> OTHER INFORMATION: Synthetic

<400> SEQUENCE: 49
tataactagt ttcgctctgt ttaaagtacc                                    30

<210> SEQ ID NO 50
<211> LENGTH: 30
<212> TYPE: DNA
<213> ORGANISM: Artificial Sequence
<220> FEATURE:
<223> OTHER INFORMATION: Synthetic

<400> SEQUENCE: 50
ataaactagt cgccgtcgct gcttatcttg                                    30

<210> SEQ ID NO 51
<211> LENGTH: 30
<212> TYPE: DNA
<213> ORGANISM: Artificial Sequence
<220> FEATURE:
<223> OTHER INFORMATION: Synthetic

<400> SEQUENCE: 51
tataactagt agtatgtgtg ttccgccaat                                    30

<210> SEQ ID NO 52
<211> LENGTH: 866
<212> TYPE: DNA
<213> ORGANISM: Artificial Sequence
<220> FEATURE:
<223> OTHER INFORMATION: Synthetic

<400> SEQUENCE: 52 gatccccac acaccatagc ttcaaaatgt ttctactcct tttttactct tccagatttt     60
ctcggactcc gcgcatcgcc gtaccacttc aaaacaccca agcacagcat actaaatttt   120
ccctctttct tcctctaggg tgtcgttaat tacccgtact aaaggtttgg aaaagaaaaa   180
agagaccgcc tcgtttcttt tcttcgtcg aaaaaggcaa taaaaatttt tatcacgttt    240 cttttcttg aaattttttt ttttagtttt tttctctttc agtgacctcc attgatattt    300
aagttaataa acggtcttca atttctcaag tttcagtttc attttttcttg ttctattaca  360 acttttttta cttcttgttc attagaaaga aagcatagca atctaatcta aggggcggtg   420
ttgacaatta atcatcggca tagtatatcg catagtata atacgacaag gtgaggaact    480
aaaccatggc caagttgacc agtgccgttc cggtgctcac cgcgcgcgac gtcgccggag   540
cggtcgagtt ctggaccgac cggctcgggt ctcccggga cttcgtggag gacgacttcg    600
ccggtgtggt ccgggacgac gtgaccctgt tcatcagcgc ggtccaggac caggtggtgc    660
cggacaacac cctggcctgg gtgtgggtgc gcggcctgga cgagctgtac gccgagtggt   720
cggaggtcgt gtccacgaac ttccgggacg cctccgggcc ggccatgacc gagatcggcg   780
agcagccgtg ggggcgggag ttcgccctgc gcgacccggc cggcaactgc gtgcacttcg    840
tggccgagga gcaggactga cacgtc                                       866

<210> SEQ ID NO 53
<211> LENGTH: 1557
<212> TYPE: DNA
<213> ORGANISM: Pichia angusta

<400> SEQUENCE: 53
atggcagtgc agggtcttgt tatccctcac tttgataaca tccctcagca gttctcgctt    60

-continued

```
gtgaaacaga caaaggaggc cgcaaagacc gaatcgcccg ctgtcaacct gttggacgag      120
accaacgcca gtccgctgat caccacgcca gttgcagtgg agaacgtcat tccaaactct      180
tacattgtcg tgttcaagtc tggtgtctcc tcagactcta ttgactttca catgagctgg      240
ctgcaagatg tgcactccca gatcgtcaac gagctgggat tgagtccaga ggaggcctct      300
gcccagggct tcaagtctga catcctcgat ttgactcacg tcttcaagat tagcgacttc      360
ttctcgggct ataccggtgt tttcccagaa gctgtcgtta accttatcag aagcacccca      420
gacgttgcat ttgtcgagat ggactctatg gtgtacgcca acgaggctga gactcagaca      480
ggtgctccat ggggattgtc gagaatctcc cacagagatg cactcagtct cggaaacttc      540
aatcaatacc tatacgatga cgtcgctggt gacggcgtca cagcatacgt cattgataca      600
ggtatcaatg tcaaccacaa ggacttcggc ggcagagcca agtggggaaa gactatccca      660
accggtgacg acgatatcga cggtaacggt cacggtaccc actgtgctgg taccatcggc      720
tccgagcact acggtgtttc gaagaacgcc aaccttgttg ccgtcaaggt tttgagatcc      780
aacggctctg gttcgatgtc tgacgtcgtc aagggtgttg agtttgctgc caacgcccac      840
attgctgagg ctaagcagaa aaagccaggc ttcaagggat ccaccgccaa catgtctctt      900
ggtggtggca agtctcctgc cttggatatg gcagtcaacg ctgcagtcaa ggctggcttg      960
cactttgccg ttgccgcagg taacgacaat gccgacgctt gcaactactc gccagccgcc     1020
gcggagaatg ctgtcactgt gggtgcctcg accttgtccg actctagagc ctacttctcg     1080
aactacggca agtgcgtgga catctttgct cctggtctca acatcttgtc tacctacatt     1140
ggctccgata ccgcaactgc tactctttct ggtacttcca tggcttctcc acacgtttgt     1200
ggtttgcttg cttactacct tggactgcaa ccagagagcg actctcagtt cgcctcgtcg     1260
tctgtttctc cagctcagct gaagaagaac atcatcaagt tggtaccaa gaatgctctt      1320 tctgacattc cagacgacgg cactccaaac gtcctgattt acaacggtgc aggtaagaac     1380
ttgactgagt tctgggacgc ggattatgag tacgagtccg atagttctct caaggtggac     1440
ttgaaccgag ctctagacat tgcttcttcc gtggagatcg acctcgacgg tttgaaggag     1500
aagtttgacg agatcctcaa cgaggttcaa agtgaagtga agtctctgtt gaactag        1557
```

```
<210> SEQ ID NO 54
<211> LENGTH: 30
<212> TYPE: DNA
<213> ORGANISM: Artificial Sequence
<220> FEATURE:
<223> OTHER INFORMATION: Synthetic

<400> SEQUENCE: 54
ataaactagt gttctcgctt gtgaaacaga                                      30

<210> SEQ ID NO 55
<211> LENGTH: 30
<212> TYPE: DNA
<213> ORGANISM: Artificial Sequence
<220> FEATURE:
<223> OTHER INFORMATION: Synthetic

<400> SEQUENCE: 55
tataactagt gcgtcccaga actcagtcaa                                      30

<210> SEQ ID NO 56
<211> LENGTH: 20
<212> TYPE: DNA
<213> ORGANISM: Artificial Sequence
```

```
<220> FEATURE:
<223> OTHER INFORMATION: Synthetic

<400> SEQUENCE: 56
gatcccccac acaccatagc                                                    20

<210> SEQ ID NO 57
<211> LENGTH: 20
<212> TYPE: DNA
<213> ORGANISM: Artificial Sequence
<220> FEATURE:
<223> OTHER INFORMATION: Synthetic

<400> SEQUENCE: 57
gacgtgtcag tcctgctcct                                                    20

<210> SEQ ID NO 58
<211> LENGTH: 1242
<212> TYPE: DNA
<213> ORGANISM: Pichia angusta

<400> SEQUENCE: 58
atgaaacttt ctctcccaac cctttactcg cttgctcttg tgcttggatt ggtctccgtg         60
gccgatgcca aggtgcacaa agctcccatc aaaaaagctc ctgcacaggc tacttaccag        120
gatgttactc tcggcgatta tgttgagtcg ttgaagcaaa agtatgttac atcttacaat        180
aagtttatcg ccgcccaaca gaatgaccag caagttatct cgctcggcaa gcgttctgac        240
gagagtgcaa cctctggaca caacactcct ttgaccaact atctcaacgc tcagtacttc        300
accgagatac aattgggcac tcctggccag tcgttcaagg ttatcctcga caccggttcc        360
tctaacctgt gggttcctag tagcgattgc tcgtctttgg cctgttactt gcatactaaa        420
tacgaccacg atgagtcctc cacttaccag aaaaacggtt cttcctttaa tattcaatat        480
ggctcgggtt ccctcgaggg ttacgtttcc aagacacac tgactattgg tgaccttgtc         540
atccctaagc aggatttcgc tgaggctact agcgaacctg gcttggcttt tgcttttgga        600
aagtttgacg gtatcctggg tctggcttac gacactatct cggtcaacag aatcgttcct        660
ccaatttaca atgctatcaa tttggaactg ctggacgccc acaattcgc attttacctt         720 ggtgacactt caaagtccga gcaggacgga ggagaggcta cctttggtgg atacgatgtg        780
tctaagtaca caggtgacat cacctggttg ccagtcagaa gaaaggctta ctgggaagtg        840
aagtttagtg gtattgccct tggtgacgaa tacgccccat ggagaatac gggagctgcc         900 attgacaccg gaacctcttt gattgctctt ccatctcaat ggctgaaat attgaactct         960 caaattggtg ccgagaagtc atggtctgga cagtaccaga tcgactgtga caagagagat       1020
tcgctgcctg acctgacttt caatttcgat ggttacaact ttaccatctc gccttacgac       1080
tacactttgg aagtttctgg ttcttgtatt tctgcattca ctccaatgga tctcccagcc       1140
ccaattggtc caatggccat cattggtgac gctttcctca gaagatacta ctccgtttat       1200
gaccttggca aagacgctgt gggattggct aaggctgtgt aa                          1242

<210> SEQ ID NO 59
<211> LENGTH: 30
<212> TYPE: DNA
<213> ORGANISM: Artificial Sequence
<220> FEATURE:
<223> OTHER INFORMATION: Synthetic

<400> SEQUENCE: 59
```
ataaactagt ggtctccgtg gccgatgcca                                        30

<210> SEQ ID NO 60
<211> LENGTH: 30
<212> TYPE: DNA
<213> ORGANISM: Artificial Sequence
<220> FEATURE:
<223> OTHER INFORMATION: Synthetic

<400> SEQUENCE: 60
tataactagt tctggtactg tccagaccat                                        30

<210> SEQ ID NO 61
<211> LENGTH: 1731
<212> TYPE: DNA
<213> ORGANISM: Pichia angusta

<400> SEQUENCE: 61
atgaaagttg ctatactgtt ttccttggct tcgagtgtct gtgttctggg agacccacag        60
tacgtcaaac tggaggcgtc tgttctgcgt ggagccacct acaaggaatc acagaagggg       120
gccaagccgt tcatgttgga aagagggct gatgacggct cggtcacgat ggaattgcag        180
aacgcacagt cttttttacca gtcgagatc gaaataggt ctgataagca aaggtgggg         240
gtgttgattg ataccggttc ctcggatttg tgggtgacga actcgaataa cacttactgt       300
tcgtcttcca gcagtaaaaa aatgaaacgg gacggatctc gcaatgtgct ccgaaaagga       360
cgcgatcttt ccgacctgta caatttcaac tctccaaacg aagacaacaa tgcaaaagca       420
ctcctgagtg ctgggggaga tctgaccaca gcagagactg taacccagga tgagacgcag       480
acggcgctcg ctgcgcaggc caccgttgac tgctcgcaat acggaacttt cgatccttca       540
acgtcggatt cgttccacaa caacggcacc aaatttgaga tttcgtacgc ggacagcact       600
tttgcccgtg aacctgggg ctacgatgat gtcactttca gtggtgtcac tgtcaacgat        660
ctctcgttgg ccgtgcaga tgaaacagat tctgcgactg tgttttttgg tatcggattc        720
agagaactgg aaaccacgta ctcaggaggt ggaccagagc attacatcta cgacaacttg       780
ccttacaaac tggtcgacca gggactcatc ggtagagcct cctattccat ctacatgaac       840
tcaagtgatt ccagcactgc ctccattctc tttggagcag tggaccaaag caagtatacc       900
ggagatcttg gcttgcttcc tatcatcaac acgttgctt cctacggtta cgaaaagccc        960
attaagcttc aaatcaccct gtctgctata acgctcacca actctaaagg gcagcaagtc      1020
agtattggtt caggagctgc tgctgcactt cttgataccg aacgactttt gacgtatgct      1080
ccaaacgagg ttgtcgagaa acttgctgaa accctggact tcgtgtacag cagctctgtc      1140
ggggcctacg tggcaagatg cgacgacgtc gagagctacg ctgtcaactt cgacttccag      1200
ggtaaagtga ttgaagctcc tttgagttcc ttcctgattg ctctacaaac aaactcggga      1260
gtagtgtcct cctactgcgc attgggtatt ttctcctcgg gagacgaaac tatcaccctc      1320
ggcgacagtt ttatgcggaa cgcctacatt gtggccgacc tcgagggata tcaaatcgcc      1380
ataggtaatg tgaacctgaa tcctggagac gaacaaattg agatcatctc aggtgactcc      1440
attccttctg cttcttcggt ttccgactac tcgaataccc ggggcgcctc tgccactgct      1500
ttggatactg acaggactac tactctggga tcggtgactg ctgtgagcga tgaaaaagtg      1560
acgtcgacca agaaggtttc gaatgttgag acaagcactt cgtccgggtc cgggtcggtt      1620
tcggagtcgt ctgggtccag ctcgaactct aacaacagcc aaggacagt aggttttagt      1680
ttgtgtgcgg ttttgtgcgc attggtgatt tctatactag ctgtttgtta g              1731

```
<210> SEQ ID NO 62
<211> LENGTH: 30
<212> TYPE: DNA
<213> ORGANISM: Artificial Sequence
<220> FEATURE:
<223> OTHER INFORMATION: Synthetic

<400> SEQUENCE: 62
ataaactagt caccgttgac tgctcgcaat                                  30

<210> SEQ ID NO 63
<211> LENGTH: 30
<212> TYPE: DNA
<213> ORGANISM: Artificial Sequence
<220> FEATURE:
<223> OTHER INFORMATION: Synthetic

<400> SEQUENCE: 63
tataactagt gcgcacaaaa ccgcacacaa                                  30
```